(12) United States Patent
Lerner et al.

(10) Patent No.: US 12,011,416 B2
(45) Date of Patent: *Jun. 18, 2024

(54) VENOUS BLOOD FLOW STIMULATOR FOR EXTRACORPOREAL THERAPY

(71) Applicant: Nuwellis, Inc., Eden Prairie, MN (US)

(72) Inventors: David Lerner, St. Paul, MN (US); David J. Haskvitz, Maple Grove, MN (US)

(73) Assignee: Nuwellis, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/463,612

(22) Filed: Sep. 8, 2023

(65) Prior Publication Data
US 2024/0108533 A1 Apr. 4, 2024

Related U.S. Application Data

(63) Continuation of application No. 17/758,265, filed as application No. PCT/US2020/070553 on Sep. 18, 2020, now Pat. No. 11,793,709.
(Continued)

(51) Int. Cl.
*A61B 5/02* (2006.01)
*A61B 5/021* (2006.01)
(Continued)

(52) U.S. Cl.
CPC ....... *A61H 9/0057* (2013.01); *A61B 5/02141* (2013.01); *A61B 5/022* (2013.01);
(Continued)

(58) Field of Classification Search
CPC ................ A61H 9/0057; A61H 9/0007; A61H 2201/0157; A61H 2201/0176;
(Continued)

(56) References Cited

U.S. PATENT DOCUMENTS 2,579,209 A 12/1951 Smith
3,403,673 A 10/1968 Macleod
(Continued)

FOREIGN PATENT DOCUMENTS

CN 206228578 U 6/2017
JP 2002065648 A 3/2002
(Continued)

OTHER PUBLICATIONS

"European Application Serial No. 20908907.7, Response filed Jul. 13, 2023 to Extended European Search Report mailed Jan. 3, 2023", 6 pages.
(Continued)

*Primary Examiner* — Tu A Vo
(74) *Attorney, Agent, or Firm* — Schwegman Lundberg & Woessner, P.A.

(57) ABSTRACT

A blood flow stimulator may help encourage blood flow in a limb of a patient. The blood flow stimulator may include a housing configured for sealing about the limb of the patient. The housing may include a sealable volume, and the sealable volume may receive the limb of the patient. The blood flow stimulator may include a seal, and the seal may be coupled with the housing. The seal may engage with at least a portion of the limb, for instance to segregate the sealable volume from a surrounding environment of the blood flow stimulator. The blood flow stimulator may include a conduit extending through the housing. The conduit mat help provide access to the sealable volume, for instance from the surrounding environment. In some examples, an adjustable stent is utilized to enhance blood flow within vasculature of a patient. A stent operator may change a size of the stent.

9 Claims, 14 Drawing Sheets

Related U.S. Application Data

(60) Provisional application No. 62/955,987, filed on Dec. 31, 2019.

(51) Int. Cl.

| | | |
|---|---|---|
| *A61B 5/022* | (2006.01) | |
| *A61H 9/00* | (2006.01) | |
| *A61M 1/14* | (2006.01) | |
| *A61M 1/34* | (2006.01) | |
| *A61M 1/36* | (2006.01) | |
| *A61M 1/16* | (2006.01) | |

(52) U.S. Cl.
CPC .......... *A61B 5/02233* (2013.01); *A61H 9/00* (2013.01); *A61H 9/005* (2013.01); *A61M 1/14* (2013.01); *A61M 1/34* (2013.01); *A61M 1/3653* (2013.01); *A61M 1/16* (2013.01); *A61M 2210/005* (2013.01); *A61M 2210/08* (2013.01); *A61M 2230/005* (2013.01); *A61M 2230/62* (2013.01)

(58) Field of Classification Search
CPC ...... A61H 2201/1207; A61H 2201/164; A61H 2201/1642; A61H 2201/1645; A61H 2201/5071; A61H 2205/06; A61H 2205/065; A61H 2205/10; A61H 2205/106; A61H 2205/12; A61H 2209/00
See application file for complete search history.

(56) References Cited

U.S. PATENT DOCUMENTS

| | | | |
|---|---|---|---|
| 3,465,748 | A | 9/1969 | Kravchenko |
| 3,487,837 | A | 1/1970 | Petersen |
| 4,299,219 | A | 11/1981 | Norris, Jr. |
| 4,664,651 | A | 5/1987 | Weinshenker et al. |
| 4,883,462 | A * | 11/1989 | Williamson ......... A61H 9/0078 601/152 |
| 4,908,013 | A | 3/1990 | Huber et al. |
| 5,301,690 | A | 4/1994 | Lewis et al. |
| 5,447,504 | A | 9/1995 | Baker et al. |
| 5,636,643 | A | 6/1997 | Argenta et al. |
| 6,026,684 | A | 2/2000 | Calder |
| 6,565,593 | B2 | 5/2003 | Diana |
| 8,226,586 | B2 | 7/2012 | Cazzini et al. |
| 8,287,474 | B1 | 10/2012 | Koenig et al. |
| 8,795,229 | B2 | 8/2014 | Bakhtyari-nejad-esfahani |
| 11,110,021 | B2 | 9/2021 | Laasanen et al. |
| 11,793,709 | B2 | 10/2023 | Lerner et al. |
| 2004/0106907 | A1 | 6/2004 | Liu |
| 2005/0159690 | A1 | 7/2005 | Barak et al. |
| 2006/0069357 | A1 | 3/2006 | Marasco |
| 2007/0015949 | A1 | 1/2007 | Kaiser |
| 2008/0021531 | A1 | 1/2008 | Kane et al. |
| 2008/0119801 | A1 | 5/2008 | Moore |
| 2009/0177184 | A1 | 7/2009 | Christensen et al. |
| 2009/0270910 | A1 | 10/2009 | Hargens et al. |
| 2011/0000484 | A1 | 1/2011 | Melsheimer |
| 2011/0201990 | A1 | 8/2011 | Franano |
| 2011/0264063 | A1 | 10/2011 | Weston |
| 2011/0288458 | A1 | 11/2011 | Jones et al. |
| 2012/0053536 | A1 | 3/2012 | Moore |
| 2012/0277787 | A1 | 11/2012 | Eggers |
| 2014/0094893 | A1 | 4/2014 | Gerber |
| 2014/0276287 | A1 | 9/2014 | Pickett et al. |
| 2015/0065931 | A1 | 3/2015 | Alnabulsi et al. |
| 2016/0128399 | A1 * | 5/2016 | Giulianotti ............ A41D 1/005 600/301 |
| 2016/0136404 | A1 * | 5/2016 | Moore .................. A61M 35/10 604/290 |
| 2017/0360649 | A1 | 12/2017 | Hisdal et al. |
| 2018/0272147 | A1 | 9/2018 | Freeman et al. |
| 2020/0093383 | A1 | 3/2020 | Arkans et al. |
| 2023/0023986 | A1 | 1/2023 | Lerner et al. |

FOREIGN PATENT DOCUMENTS

| | | |
|---|---|---|
| KR | 20090011617 U | 11/2009 |
| KR | 20120005724 U | 8/2012 |
| KR | 20130122857 A | 11/2013 |
| KR | 20160000789 U | 3/2016 |
| WO | WO-2020070553 A1 | 4/2020 |
| WO | WO-2021138624 A1 | 7/2021 |

OTHER PUBLICATIONS

"U.S. Appl. No. 17/758,265, Corrected Notice of Allowability mailed Sep. 27, 2023", 2 pgs.

"U.S. Appl. No. 17/758,265, Notice of Allowance mailed Jun. 6, 2023", 23 pgs.

"European Application Serial No. 20908907.7, Extended European Search Report mailed Jan. 3, 2023", 10 pgs.

"European Application Serial No. 209089077, Response filed Jul. 13, 2023 to Office Action mailed Jan. 20, 2023", 25 pgs.

"International Application Serial No. PCT/US2020/070553, International Preliminary Report on Patentability mailed Mar. 9, 2022", 8 pgs.

"International Application Serial No. PCT/US2020/070553, International Search Report mailed Jan. 27, 2021", 5 pgs.

"International Application Serial No. PCT/US2020/070553, Invitation to Pay Additional Fees mailed Nov. 17, 2020", 2 pgs.

"International Application Serial No. PCT/US2020/070553, Response to Written Opinion filed Oct. 29, 2021 to Written Opinion mailed Jan. 27, 2021", 27 pgs.

"International Application Serial No. PCT/US2020/070553, Written Opinion mailed Jan. 27, 2021", 10 pgs.

U.S. Appl. No. 17/758,265 U.S. Pat. No. 11,793,709, filed Jun. 30, 2022, Venous Blood Flow Stimulator for Extracorporeal Therapy.

\* cited by examiner

1400

1402
Enclosing a limb of a patient in a sealed volume of a housing of a blood flow stimulator;

1404
Generating a pressure differential in the sealed volume relative to a surround environment of the blood flow stimulator; and

1406
Operating a blood pump of a blood filtration system to pump blood through a blood circuit, wherein the blood filtration system is configured to reduce one or more plasma constituents in blood of a patient

FIG. 14

VENOUS BLOOD FLOW STIMULATOR FOR EXTRACORPOREAL THERAPY

CLAIM OF PRIORITY

This patent application is a continuation of U.S. application Ser. No. 17/758,265, filed on Jun. 30, 2022, which is a U.S. National Stage Filing under 35 U.S.C. 371 from International Application No. PCT/US2020/070553, filed on Sep. 18, 2020, and published as WO 2021/138624, which claims the benefit of priority of Lerner et al., U.S. Provisional Patent Application Ser. No. 62/955,987, filed on Dec. 31, 2019, each of which are hereby incorporated by reference herein in their entirety.

TECHNICAL FIELD

This document pertains generally, but not by way of limitation, to stimulating blood flow in a limb of a patient.

BACKGROUND

A blood filtration system may reduce one or more plasma constituents in blood of a patient. A catheter may be inserted into vasculature of the patient. Blood flowing through the vasculature of the patient may be withdrawn from the vasculature and into the catheter. Blood may flow through a blood circuit, including a filter that reduces the plasma constituents in the blood. Occlusion of the blood circuit may diminish performance of the blood filtration system.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 14 shows one example of a method for stimulating blood flow in vasculature of a patient, according to an embodiment of the present subject matter.

DETAILED DESCRIPTION

Figure 1:
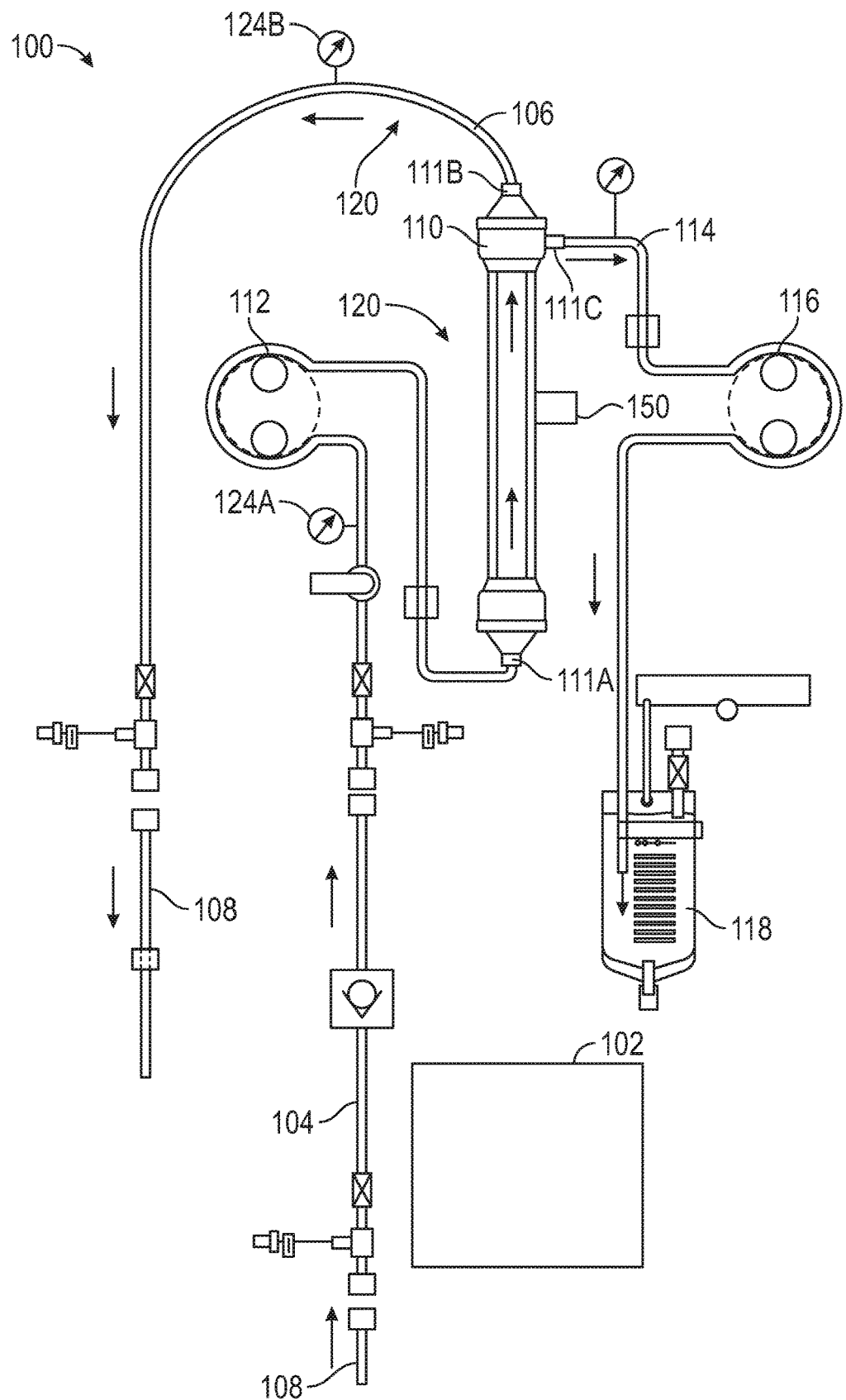
FIG. 1 shows a schematic view of an example of a blood filtration system, according to an embodiment of the present subject matter.

FIG. 1 shows a schematic view of an example of portions of a blood filtration system 100, according to an embodiment of the present subject matter.

The blood filtration system 100 may reduce one or more plasma constituents (e.g., water, proteins, electrolytes, or the like) in blood of a patient. The blood filtration system 100 may facilitate one or more blood filtration operations, including (but not limited to): extracorporeal ultrafiltration, continuing renal replacement therapy ("CRRT"), slow continuous ultrafiltration ("SCUF"), continuous veno-venous hemofiltration ("CVVH"), continuous veno-venous hemofiltration ("CVVHD"), dialysis, continuous veno-venous hemofiltration including dialysis and filtration ("CVVHDF"), sustained low efficiency dialysis ("SLED"), extracorporeal membrane oxygenation ("ECMO") therapy, modified ultrafiltration, and peripheral plasmapheresis, peripheral hemofiltration.

The blood filtration system 100 may include a controller 102. The controller 102 may include processing circuitry, for instance an integrated circuit. As described herein, the controller 102 may be configured to control one or more components of the blood filtrations system 100.

The blood filtration system 100 may include a withdrawal line 104 and may include an infusion line 106. The lines 104, 106 may be configured to couple with a catheter 108, and the lines 104, 106 may transmit blood within the blood filtration system 100. In an example, the catheter 108 may be inserted into a blood stream of the patient, for instance the catheter 108 may be inserted into a basilic vein, cephalic vein, brachial vein, the axillary vein, the subclavian vein, the brachiocephalic vein, or the like. Blood may flow into the catheter 108, into the withdrawal line 104, through other components of the system 100, through the infusion line 106, into the catheter 108, and back into the blood stream of the patient. The line 104 may be separate from the line 106. The lines 104, 106 may be in communication with the catheter 108. For example, the catheter 108 may include one or more lumens, for example a withdrawal lumen in communication with the line 104 and an infusion lumen in communication with the line 106.

The lines 104, 106 may be configured to couple with a filter 110, for instance the lines 104, 106 may include one or more fittings that facilitate coupling the lines 104, 106 with the filter 110. In an example, the withdrawal line 104 may couple with a filter inlet port 111A, and the infusion line 106 may couple with a filter outlet port 111B. The filter 110 may be configured to reduce an amount of one or more plasma constituents (e.g., water, electrolytes, or the like) in blood flowing through the filter 110 and provide a filtrate fluid including the one or more plasma constituents. As described herein, blood may flow through the lines 104, 106 to and from the catheter 108. The lines 104, 106 may be coupled with the filter and blood may flow from the withdrawal line 104, through the filter 110, and into the infusion line 106.

The blood filtration system 100 may include a blood pump 112, and the blood pump 112 may pump (e.g., convey, drive, push, or the like) blood through the blood filtration system 100. In an example, the blood pump 112 may be a peristaltic pump, and the blood pump 112 may engage with the withdrawal line 104 to pump blood through the withdrawal line 104 and into the filter 110. The controller 102 may be configured to operate the blood pump 112 to vary a speed of the blood pump 112 and accordingly vary the flow rate of blood through the blood filtration system 100 (e.g., the withdrawal line 104, the filter 110, the infusion line 106, or the like).

Referring again to FIG. 1, the blood filtration system 100 may include a filtration line 114 and a filtration pump 116. The filtration line 114 may be configured to couple with the filter 110 (e.g., with a fitting), for instance the filtration line 114 may couple with a filtrate fluid port 111C. The filter 110 may be configured to transmit the filtrate fluid (including one or more plasma constituents) extracted by the filter 110 to the filtrate fluid port 111C.

The filtration pump 116 may pump extracted filtrate fluid from the filter 110, and into a filtrate fluid reservoir 118 (e.g., a bag, container, bladder, or the like). In some examples, the filtration pump 116 may be a peristaltic pump that engages with the filtration line 114 to pump the filtrate fluid through the filtrate fluid line 114. The controller 102 may be configured to vary a speed of the filtration pump 116 and accordingly vary the flow rate of filtrate fluid through the blood filtrate system 100 (e.g., the filtration line 114).

The system 100 may include a blood circuit 120, and the blood circuit 120 may include one or more components of the system 100, such as may provide a conduit for blood flow. For example, the blood circuit 120 may include (but is not limited to) the withdrawal line 104, the infusion line 106, the catheter 108, the filter 110, the filtration line 114, the filtrate fluid reservoir 118. The blood circuit 120 may include components of the system 100 that are in communication with a biological fluid of the patient.

Figure 2:
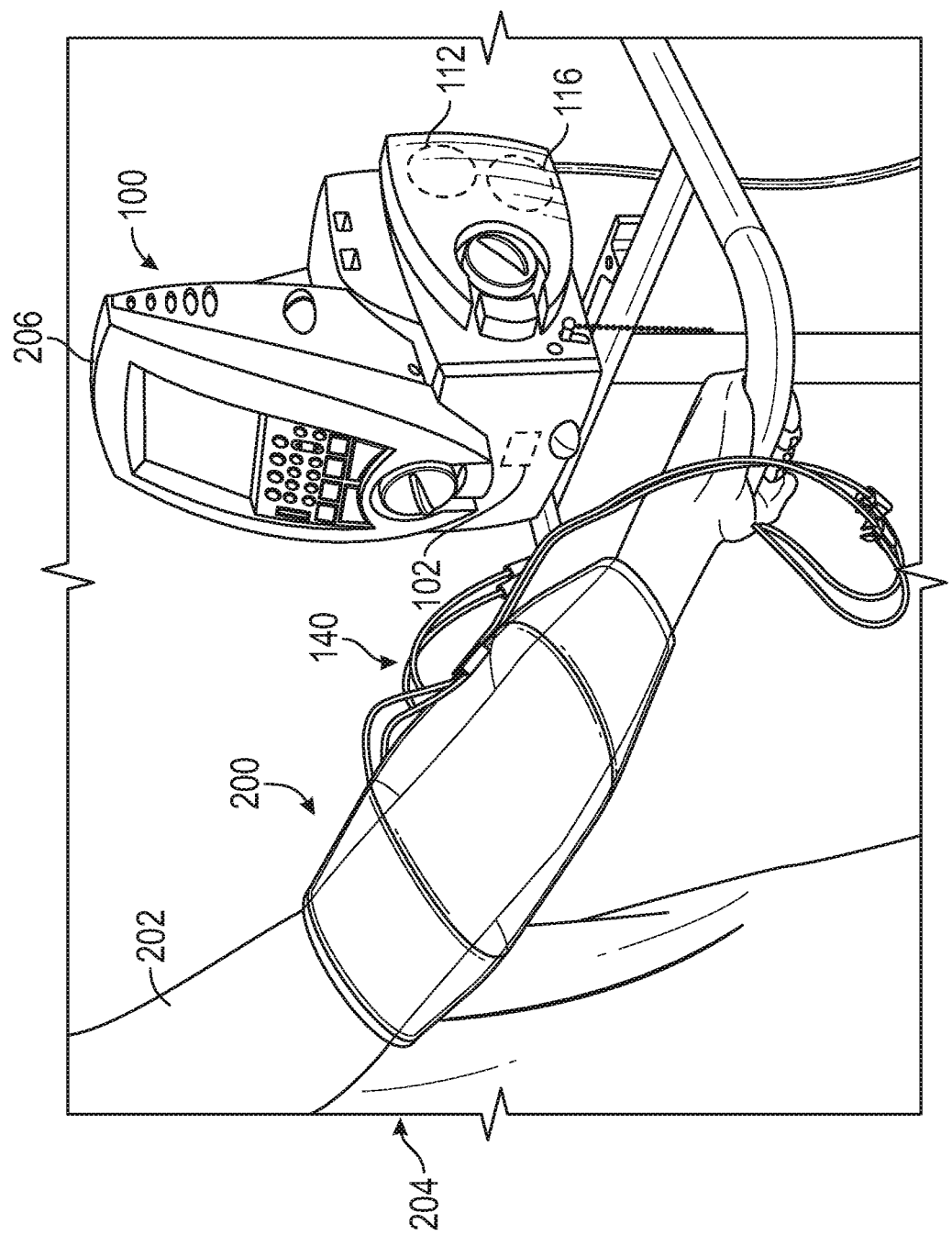
FIG. 2 shows a perspective view of an example of a blood flow stimulator, according to an embodiment of the present subject matter.

FIG. 2 illustrates a perspective view of an example of a venous blood flow stimulator 200, according to an embodiment of the present subject matter. The blood flow stimulator 200 may encourage (e.g., enhance, improve, increase, or the like) blood flow in a limb 202 of a patient 204. For example, the blood filtration system 100 may include the blood flow stimulator 200, and the blood flow stimulator 200 may encourage blood flow in the patient 204 to enhance the performance of the blood filtration system 100. Continuous blood flow through the conduit provided by the blood circuit 120 may help inhibit occlusions in the blood circuit 120. For instance, maintaining continuous blood flow through the blood circuit 120 (e.g., the catheter 108, withdrawal line 104, infusion line 106, filter 110, or the like) may help improve the lifespan of the blood circuit 120, for instance the lifespan of the filter 110 may help reduce a need for replacement of the components of the blood circuit 120. For example, the amount of time that the filter 110 may be used during blood filtration therapy may be increased when the blood flow stimulator 200 encourages blood flow in the limb 202 of the patient 204.

Figure 3:
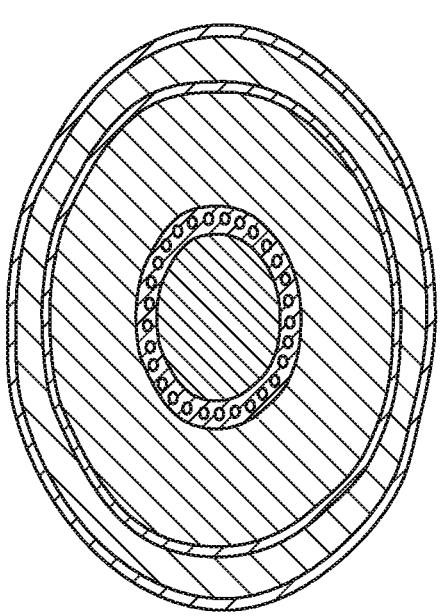
FIG. 3 shows a vein in an unconstricted configuration, according to an embodiment of the present subject matter.
Figure 4:
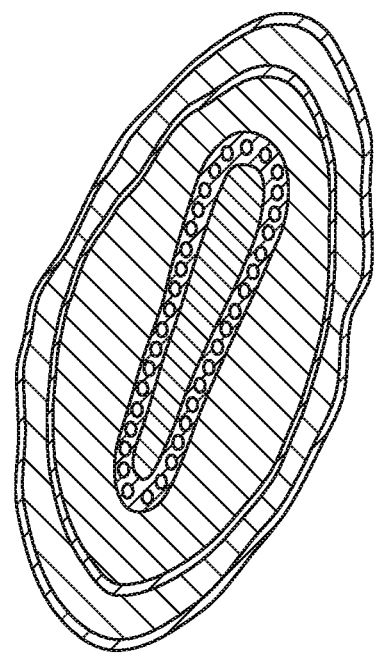
FIG. 4 shows the vein of FIG. 3 in a constricted configuration, according to an embodiment of the present subject matter.

A rate of blood flowing through a vein of the patient 204 may vary according to one or more conditions, which may cause an abnormal blood flow state and (potential) clotting in the vasculature of the patient 204 or in the blood circuit 120. For instance, occlusion of the vein (or the blood circuit 120) may reduce blood flow through the vein (or the blood circuit 120). In an example, a vein may be constricted under one or more other circumstances. For example, the patient 204 may apply pressure to the limb 202 (e.g., the patient 204 may lay on top of its arm) or move its arm (e.g., flexion, extension, or the like). The constriction of the vein may cause blood flow occlusion in the vein, or through the blood circuit 120. These and other similar maneuvers may lead to vein diameter reduction and concomitant flow limitations. FIG. 3 shows a vein 300 in an unconstricted configuration (e.g., with a first cross-sectional area). FIG. 4 shows the vein 300 in a constricted configuration (e.g., with a second cross-sectional area). The constriction of the vein 300 may reduce the flow of blood through the vein 300, for example because the constriction reduces a cross-sectional area of the vein 300. Further, blood flow through the system 100 may be affected by one or more conditions, including (but not limited to) inappropriate catheter selection, inadequate catheter placement, overly vigorous patient motion (e.g., constriction of a vein, or the like), pausing of the blood pump 112, occlusion of portions of the blood circuit 120 (e.g., within tubing, a catheter, or the like), occlusion of the catheterized vein (e.g., constriction of a vein, patient motion, or the like), inadequate anti-coagulation, blood hyper-viscosity due to hemo-concentration, hypovolemia, or the like.

In some approaches, when the withdrawn venous blood makes contact with the blood circuit 120, a potential exists for a clot to occur in the blood circuit 120. For example, blood may clot when flowing through the filter 110, and the clotting may occlude the filter 110. An occlusion in the blood circuit 120 may lead to an increase in resistance of flow of blood through the filter 110. Clotting of blood in the filter 110 may result in loss of the filter 110 (e.g., because the filter becomes clogged due to clotting of blood in the filter 110). Accordingly, clotting of the filter 110 may necessitate replacement with a new filter 110).

An anti-coagulant may be used to inhibit occlusion in the blood circuit, for instance to inhibit clots from forming in the filter 110. For example, an anti-coagulant is infused (e.g., with non-regional infusion) into the blood circuit 120. The anti-coagulant will be introduced into the circulatory system of the patient 204, for instance because the blood flowing through the blood circuit 120 is infused back into the patient 204. Introduction of anti-coagulant into the patient may result in unwanted outcomes (e.g. bleeding, heparin induced thrombocytopenia, or the like). Accordingly, the present subject matter reduces occlusion of the blood circuit 120 without requiring an anti-coagulant (or use in combination with an anti-coagulant). For instance, the blood flow stimulator 200 may encourage blood flow to reduce occlusion of the blood circuit 120.

Figure 5:
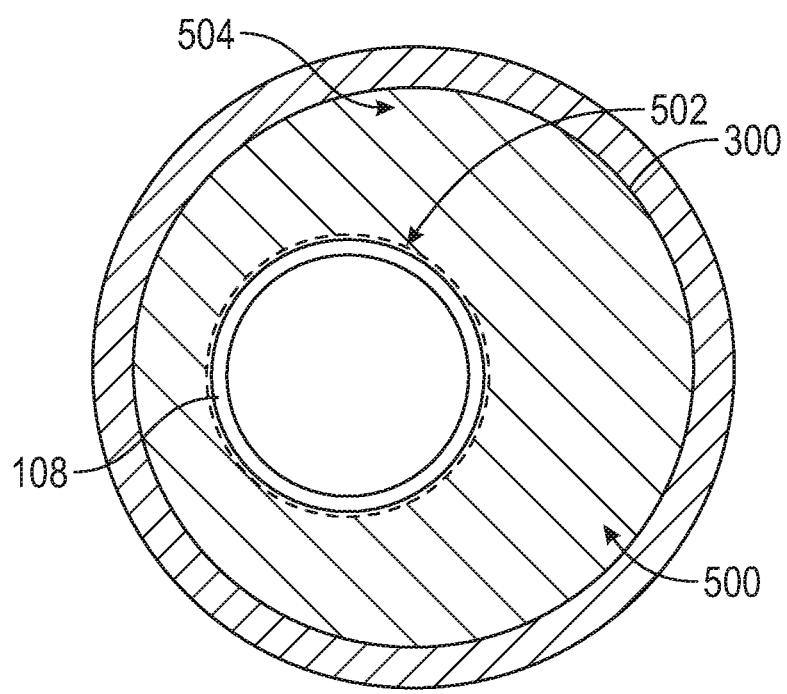
FIG. 5 shows an example of the catheter 108 located in the vein 300, according to an embodiment of the present subject matter.

FIG. 5 shows an example of the catheter 108 located in the vein 300, according to an embodiment of the present subject matter. The venous blood may be pulled into the catheter 108 (e.g., a withdrawal lumen, or the like) by the generation of negative pressure by the blood pump 112 for the blood filtration system 100. In an example, blood flows from regions distal to the catheter insertion point in the vein 300 around the outside of the catheter 108 yet within a vein lumen 500 of the vein 300. For example, the vein lumen 500 is located between an outer wall 502 of the catheter 107 and an inner wall 504 of the vein 300. Blood flow may be completely occluded if the outer diameter of the catheter 108 exceeds the diameter of the vein lumen 500 of the vein 300. Accordingly, one or more standards have been promulgated relating to the catheter lumen to vein diameter ratio, for instance to inhibit injury to the endothelial lining of the vein wall or maintain blood flow through the vein lumen 500. In an example, the catheter to vein diameter ratio may be less than 0.5 (e.g., the inner diameter of the vein lumen 500 may be at least twice as large as the outer diameter of the catheter 108).

Figure 6:
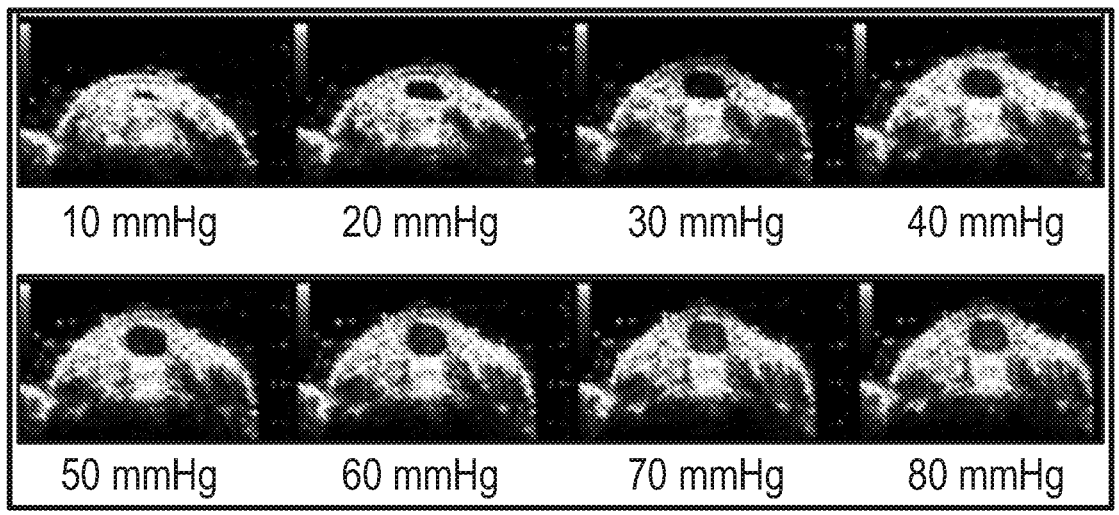
FIG. 6 shows a representation of a vein.
Figure 7:
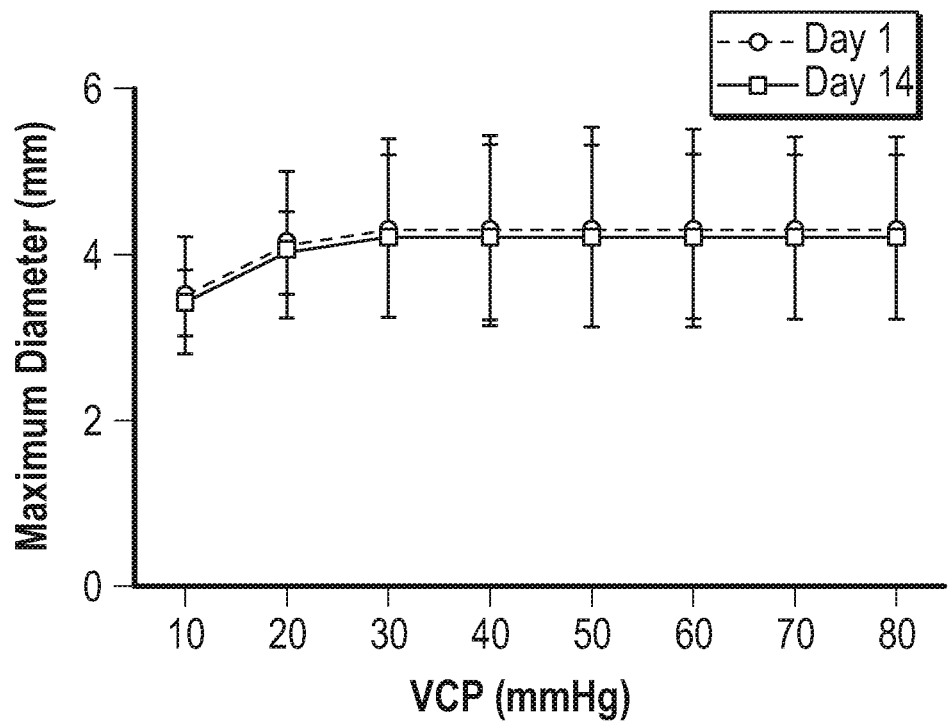
FIG. 7 shows a graph of dimensions of a vein with respect to blood pressure.

FIGS. 6 and 7 show the change in vein due to blood pressure. During blood filtration therapy (e.g., ultrafiltration to remove one or more blood constituents from the blood of a patient) venous pressure may decline and accordingly the vein diameter may decrease. As shown in FIGS. 6 and 7, vein diameter may be larger with hypervolemia, and may have a nearly circular cross section. However, for euvolemia (e.g., normal circulatory blood volume and pressure) which is the objective of the blood filtration therapy, the vein cross section has little circularity and may be less than 4 mm. A peripheral ultrafiltration catheter may be 6 Fr (e.g., 2 mm in outer diameter). Accordingly, in some approaches the vein diameter may be less than twice the diameter of the catheter 108, which may decrease flow through the blood filtration system 100 or the vasculature of the patient 204. For example, the patient 204 may be in a euvolemic state, which may be inadequate to support and sustain blood filtration therapy.

Veins may be enlarged (e.g., stretched, expanded, or the like) to a larger size, for instance due to excess blood volume causing an elevated venous pressure. In another example, vein diameter may be increased by applying a negative pressure to the outside of the arm (e.g., with the blood flow stimulator 200). Some approaches use regional heating to promote vasodilation/venodilation, for example to increase the aforementioned vein lumen 500 and promote the maintenance of blood flow around the catheter 108. Another approach includes peristaltic massaging of the distal limb 202 to promote venous flow. Peristaltic massaging may augment flow around the outside of the catheter 108 if there was no volume space at all (e.g., if the vein was completely occlude/wedged by the catheter).

The blood flow stimulator 200 may provide or increase the volume space between the outer wall 502 catheter 108 and the inner wall 504 of the vein lumen 500 (shown in FIG. 5). The increase in volume of the vein lumen 500 may increase the volume (e.g., annular area, cross-sectional area, or the like) for blood to flow from distal limb regions in a proximal direction and to the withdrawal lumen of the catheter 108. Accordingly, blood flow in the vein 300 (and the blood circuit 120) is enhanced by the blood flow stimulator 200. Thus, performance of the blood filtration system 100 is enhanced, for instance because the enhanced flood flow through the blood circuit decreases occlusions in the blood circuit 120.

Referring again to FIG. 2, the blood filtration system 100 includes the blood circuit 120 and the blood flow stimulator 200. The blood filtration system 100 optionally includes a console 206, and the console 206 may include a user interface. The console 206 may include one or more components of the blood filtration system 100. For instance, the pumps 112, 116 may be included in the console 206. The filter 110 may be replaceable in the console 206. The controller 102 may be included in the console 206.

Figure 8:
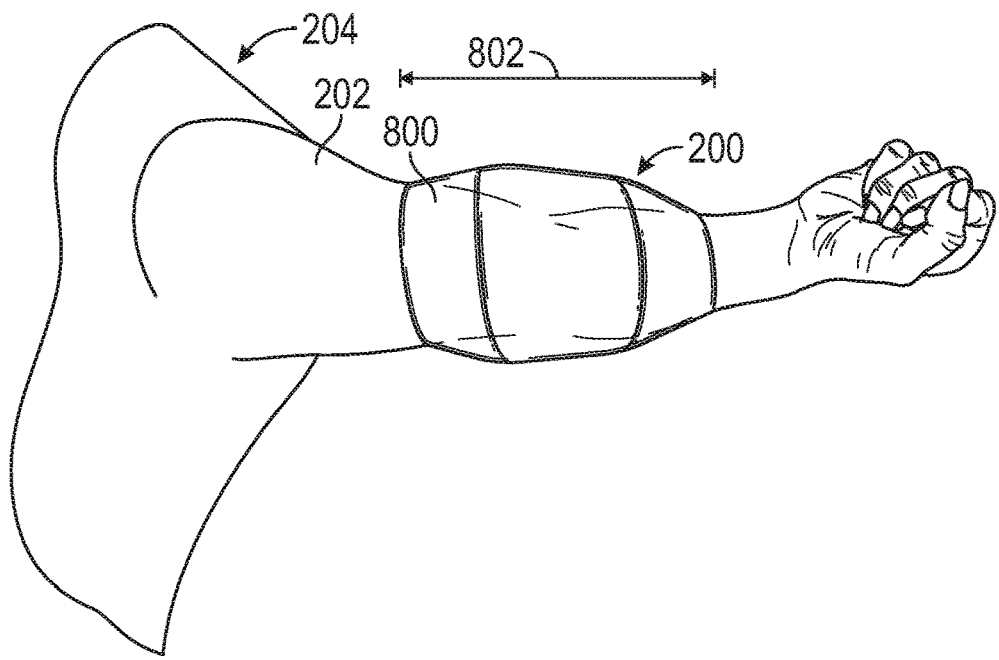
FIG. 8 shows another perspective view of the blood flow stimulator, according to an embodiment of the present subject matter.

FIG. 8 shows another perspective view of the blood flow stimulator 200, according to an embodiment of the present subject matter. The blood flow stimulator 200 provides a partly or fully sealed volume around a limb 202 (e.g., an arm, leg, or the like). The blood flow stimulator facilitates venous blood flow, for example during extracorporeal therapy or intracorporeal therapy with the blood filtration system 100.

In an example, the blood flow stimulator 200 may include a housing 800 (e.g., a shell, frame, enclosure, case, container, skeleton, or the like). The housing 800 may receive the limb 202. In an example, the two ends of the housing 800 allow for insertion of the limb 202 along a length axis 802 of the housing 800. The housing 800 may extend along the limb 202, for example from the cubital fossa to inferior to the shoulder of the patient 204. The housing 800 may be rigid (e.g., a high durometer, or the like), for example to facilitate generating a pressure differential (e.g., a vacuum, or the like) within the blood flow stimulator 200. The housing 800 may have cylindrical profile, or a different profile (e.g., one or more of cross-section, shape, size, dimensions, contour, radius, perimeter, circumference, outline, boundary, configuration, pattern, arrangement, thickness or the like) than a cylinder, for instance a rectangular cross section or the like.

Figure 9:
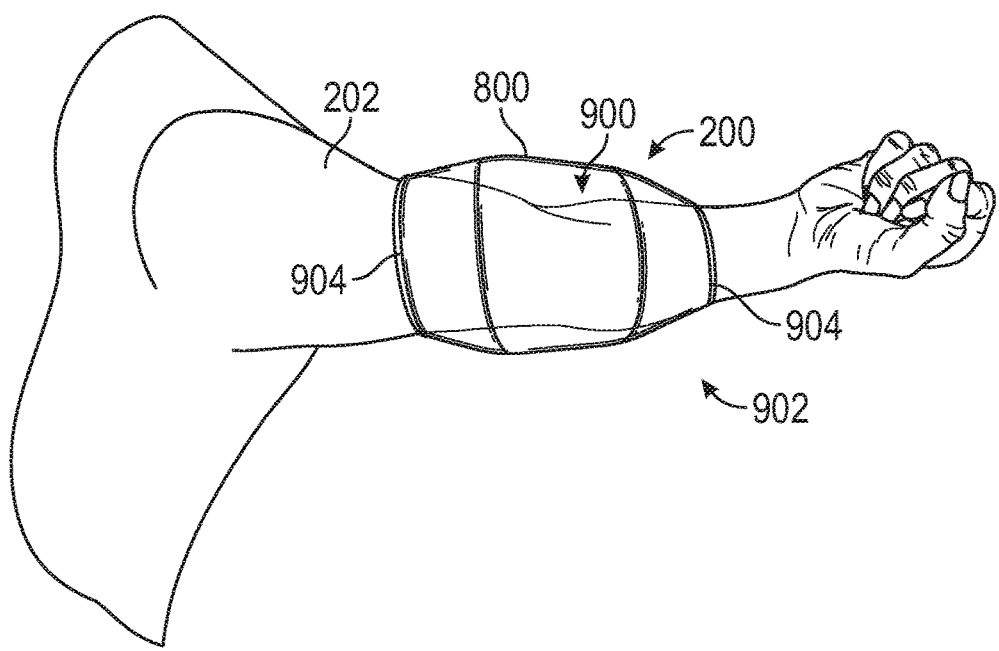
FIG. 9 illustrates yet another perspective view of the blood flow stimulator, according to an embodiment of the present subject matter.

FIG. 9 illustrates yet another perspective view of the blood flow stimulator 200, according to an embodiment of the present subject matter. Portions of the blood flow stimulator 200 are hidden in FIG. 9 for clarity (e.g., the housing 800 is translucent, or the like). The blood flow stimulator 200 includes a sealable volume 900. For instance, the housing 800 provides the sealable volume 900, and the sealable volume 900 (e.g., a chamber, pocket, cavity, enclosure, or the like) is segregated from a surrounding environment 902 (e.g., a room, space, or the like where the blood flow stimulator 200 is located). A portion of the limb 202 may be located in the sealable volume 900, for instance when the limb 202 is received in the housing 800. Accordingly, the portion of the limb 202 located in the sealable volume 900 may be segregated from the surrounding environment 902 by the blood flow stimulator 200.

In an example, the blood flow stimulator 200 includes at least one seal 904. For instance, the seal 904 may include a compliant material (e.g., a low durometer material, gasket, or the like) that engages with the limb 202 of the patient 204. The seal 904 may provide a partial (or total) hermetic seal between the limb 202 and the housing 800 of the blood flow stimulator 200. The seal 904 may segregate (e.g., isolate, segment, separate, insulate, or the like) the sealable volume 900 from the surrounding environment 902. Thus, the seal 904 may facilitate pneumatic segregation of the sealable volume 900 from the surrounding environment 902. For instance, the engagement between the seal and the limb 202 segregates the sealable volume 900 from the surrounding environment 902. Accordingly, the sealable volume 900 may have a different pressure than the surrounding environment 902. For example, the seal 904 inhibits air from entering (or leaving) the sealable volume 900.

Figure 10:
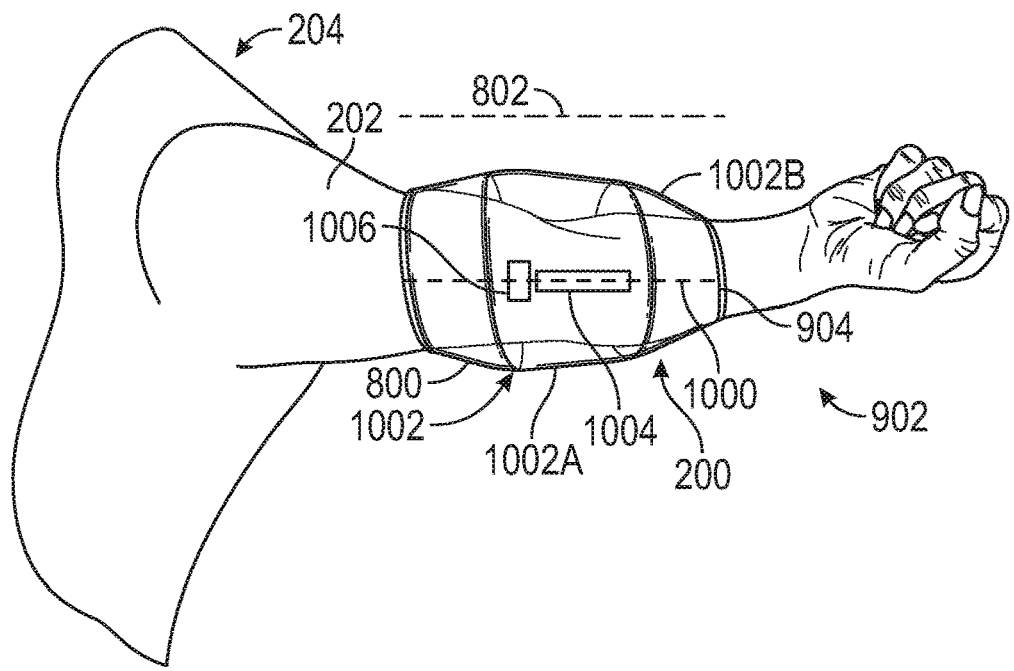
FIG. 10 shows a perspective view of another example of the blood flow stimulator, according to an embodiment of the present subject matter.

FIG. 10 shows a perspective view of another example of the blood flow stimulator 200, according to an embodiment of the present subject matter. In an example, the housing 800 opens along at least one seam 1000, for instance along the length axis 802 of the housing 800. The housing 800 may include an open configuration that facilitates locating the limb 202 in the housing 800. In this example, the housing 800 opens along the seam 1000 and the limb 202 may be placed within the housing 800. The housing 800 may transitioned to a closed configuration. In the closed configuration, the seal 904 may engage with the limb 202, and the limb 202 (or a portion of the limb 202) may be located within the sealable volume 900. Accordingly, the housing 800 may open and close to facilitate reception of the limb 202 by the housing 800.

In some examples, the housing 800 includes one or more housing segments 1002. For instance, a first housing segment 1002A may be interconnected (e.g., coupled with, attached to, or the like) a second housing segment 1002B. Optionally, a hinge 1004 interconnects the first housing segment 1002A with the second housing segment 1002B. The hinge 1004 facilitates opening and closing the housing around the limb 202 of the patient 204, for instance by allowing relative motion between the housing segments 1002.

The blood flow stimulator 200 optionally includes a locking mechanism 1006. The locking mechanism 1006 facilitates maintenance of the housing 800 in a locked configuration (e.g., with the housing 800 in the closed configuration). For instance, the locking mechanism 1006 may secure the first housing segment 1002A together with the second housing segment 1002B to maintain the housing in the closed configuration. The locking mechanism 1006 may include a latch, a catch, bolt, magnet, or the like.

Figure 11:
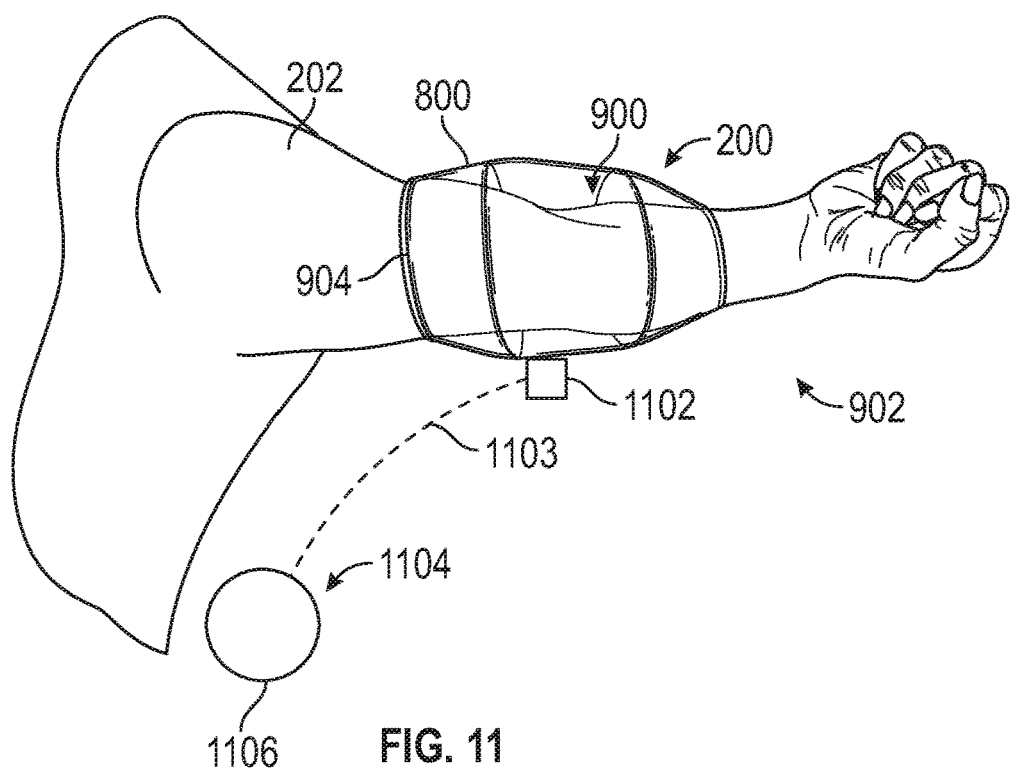
FIG. 11 shows still yet another example of the blood flow stimulator, according to an embodiment of the present subject matter.

FIG. 11 shows still yet another example of the blood flow stimulator 200, according to an embodiment of the present subject matter. In some examples, the blood flow stimulator 200 includes a conduit 1102 (e.g., a port, valve, passageway, fitting, coupling, or the like) that facilitates access to the sealable volume 900 from the surrounding environment 902. For instance, the conduit 1102 may extend through the housing 800. The conduit 1102 may be in communication with the sealable volume 900. The conduit 1102 may be located on an end of the blood flow stimulator 200, or along an outer surface of the blood flow stimulator 200.

The conduit 1102 may be connected via a hose 1103 (e.g., a tube, line, fluid channel, or the like) to a force generator 1104. The conduit 1102 may be in communication with the force generator 1104. The force generator 1104 may generate a force upon the limb 202 when the limb 202 is received in the sealable volume. For instance, the force generated by the force generator 1104 may act upon a surface of the skin of the patient 204. In an example, the force generator 1104 generates a vacuum within the sealable volume 900, and the vacuum acts upon the limb 202 to enhance blood flow within the limb 202.

In an example, the force generator 1104 includes a blood flow stimulator pump 1106 (e.g., a diaphragm pump, a swing piston pump, bellows pump, syringe pump, or the like) that generates a pressure differential between the sealable volume 900 and the surrounding environment 902. For instance, the pump 1106 may generate a pressure differential in the sealable volume 900, such as by generating a negative pressure differential with respect to the surrounding environment 902. Optionally, the pump 116 is coupled with the housing 800, and the pump 116 is in communication with the conduit 1102 (and the sealable volume 900). The pump may pump a gas, or a liquid to generate the pressure differential in the sealable volume. The blood flow stimulator 200 may include mechanical, electromechanical, piezoelectric, or other components that facilitate generating a pressure differential in the sealable volume. In another example, a bladder is in communication with the sealable volume 900. The bladder is displaced (e.g., expanded, contracted, or the like) to generate a pressure differential in the sealable volume.

As described herein, the sealable volume 900 is segregated from the surrounding environment 902. The force generator 1104 generates a pressure differential between the sealable volume 900 and the surrounding environment 902. As air (or other fluid) is evacuated from the sealable volume 900 (e.g., between the inside of the housing 800 and the limb 202), the blood flow stimulator 200 will provide a negative pressure to the limb relative to the internal limb pressure. For example, the skin surface may pull away from its resting position and the vein wall may be acted upon along 360° of its longitudinal axis due to the negative pressure in the sealable volume 900.

The catheter 108 may be located in the sealable volume 900 of the blood flow stimulator 200, for example when the stimulator 200 is in the closed (or locked) configuration. For instance, the catheter 108 may be located in the sealable volume while inserted into the vein 300 within the limb 202. In an example, the catheter may be placed along the axis 802 of the blood flow stimulator 200. The catheter 108 (e.g., including the lines 104, 106 in communication with the catheter 108) may exit near one of the ends 1200, 1202 (shown in FIG. 12) of blood flow stimulator 200. Accordingly, the catheter 108 and the lines 104, 106 may be received in the blood flow stimulator 200 to facilitate removal of one or more plasma constituents from the blood of the patient 204. In some examples, the conduit 1102 may receive catheter 108 (or the lines 104, 106) to facilitate reception of the catheter 108 in the sealable volume 900. Accordingly, the blood flow stimulator 200 facilitates interconnection of the catheter 108 with other components of the blood filtration system 100 (e.g., the pumps 112, 116).

In an example, the catheter 108 within the vein 300 is not affected by the pressure differential generated in the sealable volume 900, for instance because the rigidity of the catheter 108 resists deformation caused by forces from the pressure differential in the sealable volume 900. Optionally, the catheter 108 includes a stainless-steel coil embedded in its wall, for instance to enhance rigidity of the catheter 108 in order to help inhibit kinking, compressive occlusion, or effects from the pressure differential generated by the blood flow stimulator 200. However, the catheter 108 may include other components to impart rigidity to the catheter 108.

The blood flow stimulator 200 may provide or increase the volume space between the outer wall 502 catheter 108 and the inner wall 504 of the vein lumen 500 (shown in FIG. 5). The increase in volume of the vein lumen 500 may increase the volume (e.g., annular area, cross-sectional area, or the like) for blood to flow from distal limb regions in a proximal direction and to the withdrawal lumen of the catheter 108. For example, the force generator 1104 may be operated to increase volume space of the vein lumen 500 with the blood flow stimulator 200 to allow blood to flow around the outside of the catheter 108 yet within the vein 300. Accordingly, blood flow in the vein 300 (and the blood circuit 120) is enhanced by the blood flow stimulator 200. Thus, performance of the blood filtration system 100 is enhanced, for instance because the enhanced flood flow through the blood circuit decreases occlusions in the blood circuit 120.

Figure 12:
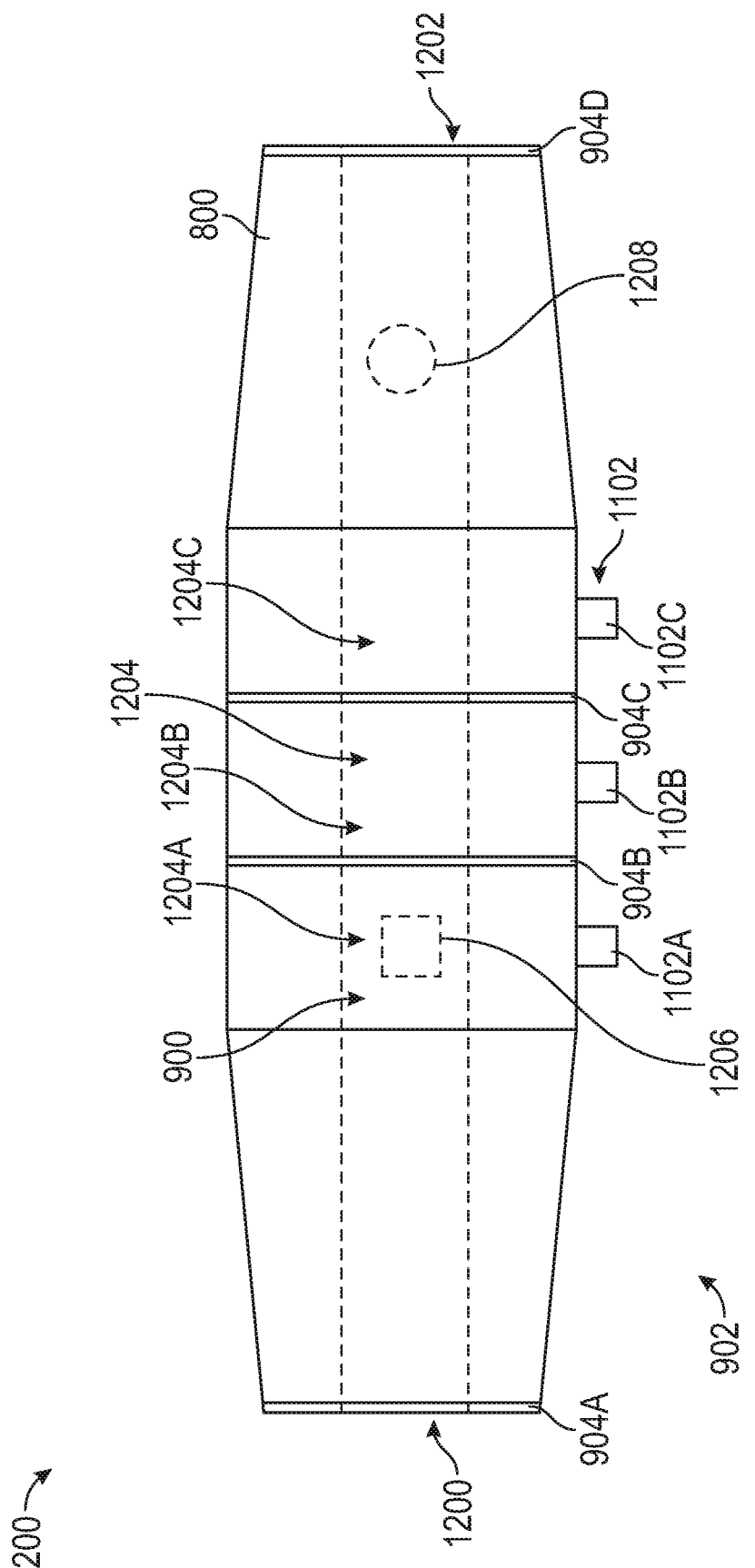
FIG. 12 shows a schematic view of still yet another example of the blood flow stimulator, according to an embodiment of the present subject matter.

FIG. 12 shows a schematic view of still yet another example of the blood flow stimulator 200, according to an embodiment of the present subject matter. The blood flow stimulator 200 may include a first end 1200 and a second end 1202. The housing 800 may extend between the ends 1200, 1202 of the blood flow stimulator 200.

The blood flow stimulator 200 may include one or more sections 1204 of the sealable volume 900. For example, the seals 904 may facilitate segregation of the sections 1204 of the sealable volume 900. In an example, a first section 1204A of the sealable volume 900 may be located between a first seal 904A and a second seal 904B. A second section 1204B may be located between the second seal 904B and a third seal 904C. A third section 1204C may be located between the third seal 904C and the fourth seal 904D. The sections 1204 may be segregated from each other. In an example, the first section may be segregated from the second section 1204B. For instance, the seals 904 may facilitate pressurizing the sealable volume 900 at a first pressure in the first section 1204A. The sealable volume 900 may be pressurized at a second pressure in the second section 1204B, for example while the first section 1204A is pressurized at the first pressure. The sealable volume 900 may be pressurized at a third pressure in the third section 1204C, for example while the first section 1204A is pressurized at the first pressure. Accordingly, the sections 1204 of the sealable volume 900 may be pressurized independent of each other (and independent of the surrounding environment 902).

The conduits 1102 may facilitate pressurizing the sections 1204 of the sealable volume 900 independent of each other. For instance, a first conduit 1102A may be in communication with the first section 1204A of the sealable volume 900. A second conduit 1102B may be in communication with the second section 1204B of the sealable volume 900. A third conduit 1102C may be in communication with the third section 1204C of the sealable volume 900. The conduits 1102 may be in communication with the force generator 1104 (shown in FIG. 11), and the force generator 1104 may generate a pressure differential in the sections 1204 of the sealable volume 900.

In some examples, the increase in vein diameter and cross-sectional area provided by the blood flow stimulator 200 provides a negative pressure to the limb 302 which causes an increase in the distal to proximal pressure gradient that (in part) drives venous return through the vein 300. This distal-proximal pressure gradient may be augmented by using one or more of the conduits 1102. For instance, pressure generated in each section 1204 may vary, for example by increasing in magnitude (e.g., total pressure decreases) from the first end 1200 (e.g., distal end) to the second end 1202 (e.g., proximal end) locations in order to apply a force to the limb 202 of the patient 204 (shown in FIG. 8) and increase the pressure gradient that drives venous return through the vein 300. Accordingly, the blood flow stimulator augments the venous return through the vein 300, for instance to enhance blood flow through the vein 300 (and into the blood circuit 120).

The blood flow stimulator optionally includes an adhesive 1206, and the adhesive 1206 may be used in place of (or in combination with) the pressure differential generated in the sealable volume 900. For example, the adhesive 1206 (e.g., a biocompatible medical adhesive, hook and loop fastener, tape, or the like) may be applied to the limb 202 (shown in FIG. 2). The blood flow stimulator 200 may displace a section 1204 of the sealable volume 900 to increase the dimensions of the vein 300 of the patient 204. In an example, the blood flow stimulator may pull on skin (e.g., a surface of the skin) of the limb 202, for instance to increase limb and vein diameter. In yet another example, one or more suction cups 1208 (e.g., with or without a gel to optimize surface contact and sealing) may be attached to the limb. The suction cups 1208 may be included in the blood flow stimulator 200, and placed around the limb 202. A mechanical or electromechanical device (e.g., an actuator, linkage, or the like), such as may include the force generator 1104 may engage with the suction cups 1208, for instance to pull on the skin of the limb 202 and increase the diameter of the vein 300 (and limb 202). Accordingly, the force generator 1104 (shown in FIG. 11) may cooperate with one or more of the adhesive 1206, the suction cups 1208, or the like to increase the diameter of the vein 300.

Figure 13:
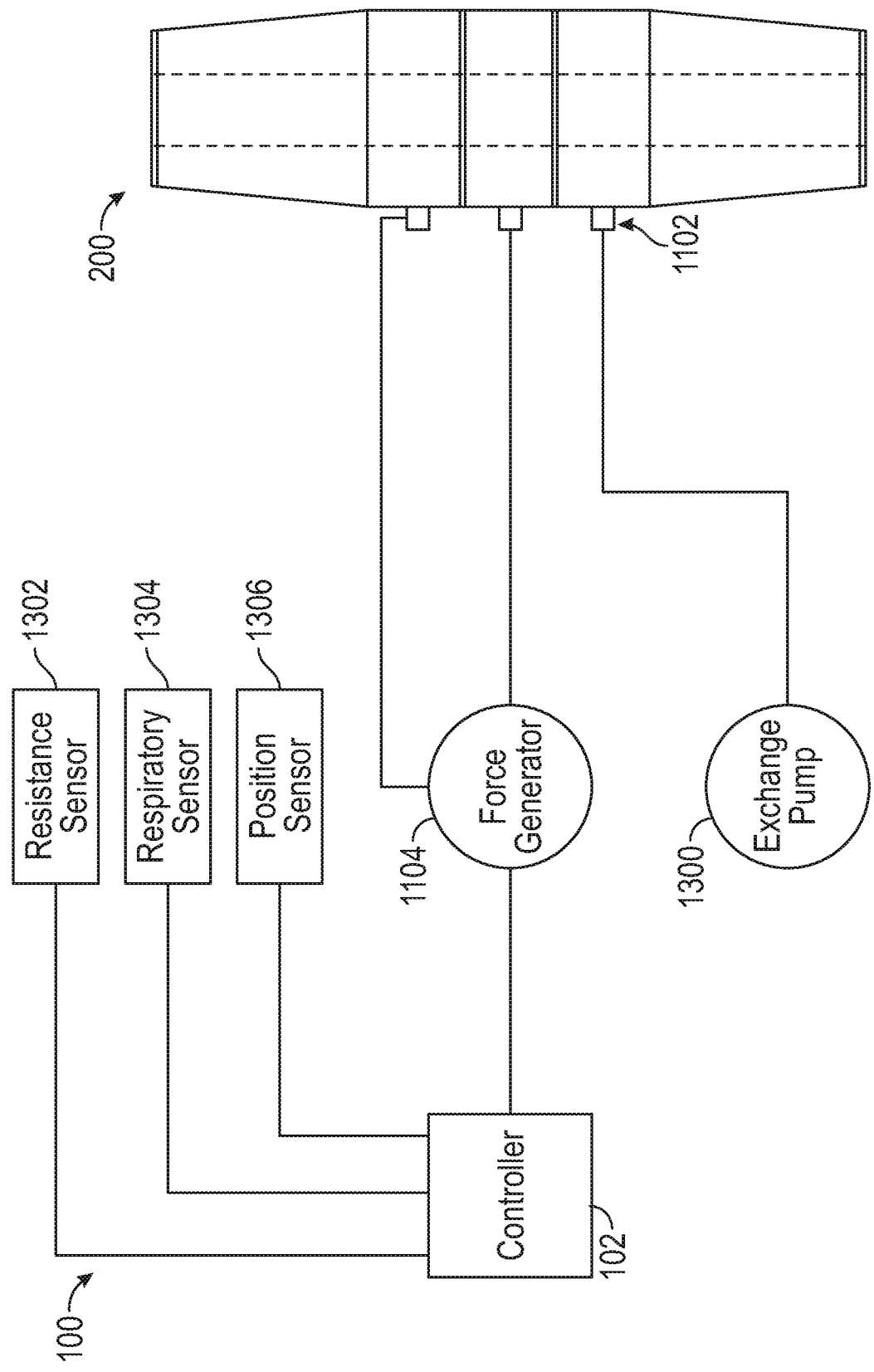
FIG. 13 shows a block diagram of the blood filtration system including the blood flow stimulator, according to an embodiment of the present subject matter.

FIG. 13 illustrates a block diagram of the blood filtration system 100 including the blood flow stimulator 200, according to an embodiment of the present subject matter. The controller 102 may operate the blood flow stimulator 200 to encourage blood flow in the patient 204 (shown in FIG. 2). For example, the controller 102 may operate the force generator 1104 to generate a pressure differential within the sealable volume 900 of the blood flow stimulator 200. In an example, the controller 102 operates the force generator 1104 to maintain a pressure differential in the sealable volume 900 (or apply a force to the patient in the sealable volume 900) for a specified time period.

The controller 102 may modulate the force generator 1104 in correspondence with one or more physical or physiological parameters (e.g., separately or in combination). The parameters include, but are not limited to venous access resistance, extracorporeal blood flow, intracorporeal blood flow, withdrawal pressure, infusion pressure, respiratory state, and real time ultrasound imaging of vein diameter, flow, or cross-sectional area. Using one or more of the aforementioned parameters, the timing, magnitude, and continuity (e.g., constant, periodic, step functions, or the like) of the force applied to the limb 202 by the blood flow stimulator 200 may be controlled (e.g., by the controller 102 of the blood filtration system 100) to optimize blood flow through the blood filtration system 100. For example, the force generator 1104 may be operated (e.g., for a given extracorporeal blood pump setting) when the withdrawal pressure exceeds a pressure threshold. The pressure threshold may include when the pressure exceeds (e.g., decreases below, equals, or increases above) a specified value (e.g., indicating flow obstruction within the vein 300 or catheter 108). For example, the force generator 1104 is operated to increase the vacuum in the sealable volume 900 (e.g., by decreasing pressure in the sealable volume 900 relative to a surrounding environment). The increase in the vacuum within the sealable volume 900 helps enhance availability of blood to flow from the patient and into the catheter 108.

In another example, the controller may operate the force generator 1104 to generate a pressure differential when a withdrawal resistance (e.g., withdrawal pressure divided by withdrawal blood flow rate) exceeds a resistance threshold. For instance, the controller 102 may operate the force generator 1104 when the rate of change of the withdrawal resistance exceeds the resistance threshold. Accordingly, the blood flow stimulator facilitates an increase in volume space within vein 300 of the patient to allow blood to flow around the outside of the catheter 108 yet within the vein 300.

The controller 102 may maintain an optimal venous access resistance during blood filtration therapy, for instance ultrafiltration (UF) to remove one or more blood constituents. If the access resistance increases (for instance when enough plasma water has been removed from the patient's circulatory system and there is very little volume space between the inner surface of the vein and outer surface of the catheter), the controller 102 may operate the force generator 1104 (or the stent 1600, shown in FIG. 16) to decrease the access resistance by increase blood flow in the vein 300 (and into the catheter 108).

The system 100 may include a resistance sensor 1302 (e.g., a pressure sensor, or the like) configured to measure and report the access resistance (e.g., a pressure sensor, or the like). The controller 102 may determine the access resistance based on measurements provided by one or more sensors, for instance a pressure sensor in communication with one or more of the lines 104, 106. The controller 102 may compare the determined access resistance with an access resistance threshold. The controller 102 may operate the force generator 1104 when the determined access resistance exceeds the access resistance threshold. The system 100 may include or more components, features, functions, or the like of the subject matter discussed in PCT application PCT/US2019/069130, which is hereby incorporated by reference herein in its entirety.

For example, FIG. 1 shows the withdrawal line 104 may be in communication with a characteristic sensor 124A and the infusion line 106 may be in communication with a characteristic sensor 124B. The sensors 124A may determine pressure in the withdrawal line 104, and the sensor 124B may determine pressure in the infusion line 106. The sensors 124A, 124B may be in communication with the controller 102, and the controller 102 may determine the pressure in the lines 104, 106 using the sensors 124A, 124B.

When the controller 102 operates the blood pump 112, the blood pump 112 generates a negative pressure in withdrawal line 104 to withdraw blood from the vasculature where the catheter tip 130 is located. The blood pump 112 may generate a positive pressure in the infusion line 106 to infuse blood into the vasculature where the catheter tip 130 is located. The magnitude of the pressure in lines 104, 106 may increase to correspondingly increase the blood flow rate within the lines 104, 106.

The blood circuit 120 (including the lines 104, 106) may have a total resistance characteristic that corresponds to an amount of resistance in the blood circuit 120 to the flow of blood through one or more components of the blood circuit, for instance the lines 104, 106 or the filter 110. One or more characteristics may contribute to the total resistance characteristic of the lines 104, 106. For example, the resistance characteristic of the lines 104, 106 may increase due to occlusion (e.g., clotting, obstruction, or the like) of the blood circuit 120 (e.g., in or around the catheter 108), changes to the vasculature (e.g., inflammation of walls of the vasculature, compression of the vasculature, or the like), hemoconcentration of the blood, or the like. The resistance characteristic (e.g., transverse or longitudinal) of the filter 110 may contribute to the total resistance characteristic of the blood circuit 120.

An increase in the resistance characteristic of the lines 104, 106 (or other components of the blood circuit 120) may diminish blood flow through the lines 104, 106. The resistance characteristic of the lines 104, 106 may be referred to as access resistance. The diminished blood flow due to the increase in the resistance characteristic of the lines 104, 106 may reduce the performance of the system 100, for example by reducing the maximum blood flow rate through the blood circuit 120 or the rate that the one or more blood constituents may be removed from the blood by the filter 110. The resistance characteristic of the lines 104, 106 may increase to the point where the blood pump 112 is unable to maintain flow within the lines 104, 106 (e.g., because the forces resisting flow in the lines exceeds the forces generated by the blood pump 112). Accordingly, an increase in the resistance characteristic of the lines 104, 106 may diminish the performance of the blood filtration system 100.

The system 100 may determine a total resistance characteristic for one or more components of the blood circuit 120, for example the withdrawal line 104 and the infusion line 106. In an example, a withdrawal line resistance characteristic may correspond to the resistance in the withdrawal line 104 to the flow of blood through the withdrawal line 104. The withdrawal line resistance characteristic may correspond to the pressure in the withdrawal line 104 divided by the actual blood flow rate of system 100 (e.g., as determined by a flow sensor). The actual blood flow rate of the system 100 may vary from a set point that the controller 102 operates the blood pump 112 at. For example, the resistance characteristic of the lines 104, 106 may reduce the actual blood flow rate through the blood circuit 120 because the resistance to the flow of blood in the lines 104, 106 decreases the efficiency of the blood pump 112.

The infusion line resistance characteristic may correspond to the resistance in the infusion line 106 to the flow of blood through the infusion line 106. The infusion line resistance characteristic may correspond to the pressure in the infusion line 106 divided by the difference between the actual blood flow rate and the filtration rate of the system (e.g., as determined by controller 102 in communication with the sensors 124). An increase in the magnitude of the resistance characteristic of the blood circuit 120 (including the lines 104, 106) may increase the force necessary to withdraw blood from (or infuse blood into) the patient by the blood pump 112. The increase in the magnitude of the resistance characteristic of the blood circuit 120 may result in (or be an indication of) clotting in the blood circuit 120. The blood flow stimulator may be modulated according to one or more of the characteristics of the blood circuit 120.

In yet another example, the phase of the respiratory cycle of a patient 204 may be monitored (e.g. end inspiration, end expiration, or other phase), for example with respiratory monitor (e.g., a sensor utilizing one or more of bioimpedance plethysmography, pneumatic plethysmography, photoelectric plethysmography, pulse oximetry, strain gage plethysmography, spirometry, or the like). The force applied to the limb 202 may be synchronized to the monitored respiratory phase (e.g., using the controller of the blood filtration system). For instance, the blood filtration system 100 may include a respiratory sensor 1304. The respiratory sensor 1304 may determine a respiratory cycle of the patient 204. For instance, the respiratory sensor 1304 may determine when the patient 204 inhales or exhales (e.g., a point in time when the patient stops inhaling). The controller 102 may be in communication with the controller 102, and the controller 102 may monitor the respiratory cycle of the patient.

The controller 102 may modulate the force generator 1104 in correspondence with the respiratory cycle of the patient 204. For example, the controller 102 may operate the pump 1106 to increase the pressure differential between the surrounding environment 902 and the sealable volume 900 during inspiration (e.g., inhalation, or the like) to augment the positive effect of inspiration on venous return. The controller 102 may modulate the pump 1106 to decrease the pressure differential on expiration (e.g., exhalation, or the like). Accordingly, the controller 102 may modulate the force applied to the skin of the patient 204. Thus, venous return may be maximized during end-inspiration, for example by increasing blood flow with the blood flow stimulator 200 and augment venous return.

The pressure differential may be periodically cycled (e.g. turned on and off or its magnitude raised and lowered) independent of other physical or physiological parameters. For example, the controller 102 may operate the force generator 1104 to for latency in effect of the blood flow stimulator 200 on the patient 204 (e.g., lag time, or the like). For instance, the controller 102 may compensate for the latency between maximizing the pressure differential in the sealable volume 900 and when the pressure differential augment blood flow in the vein 300.

The controller 102 may control the rate, magnitude, timing, periodicity, and other aspects of the force generator 1104, including incorporation of time periods during which no pressure differential is generated. The controller 102 may operate on a predictive basis (e.g., on a timed schedule) or based on feedback from physiological or anatomical parameters. For example, as blood filtration therapy (e.g., ultrafiltration, or the like) proceeds, the blood of the patient 204 becomes more hemo-concentrated (e.g., hematocrit of the blood increases). Hematocrit of the blood may be determined, for example with an optical sensor that measures hematocrit of blood in the blood circuit 120. When hematocrit increases, the viscosity of the blood increases. The resistance to blood flow in a vessel or cylindrical conduit is directly proportional to the viscosity of the fluid. Thus, the controller 102 may operate the force generator 1104 based on the determined hematocrit value of a patient. For instance, the controller 102 may operate the force generator 1104 when the determined hematocrit exceeds a hematocrit threshold.

The blood flow stimulator 200 may facilitate fluid exchange between the limb 202 located in the sealable volume 900 and the surrounding environment 902 (shown in FIG. 9). The fluid exchange provided by the blood flow stimulator 200 may enhance patient comfort, and may enhance health of the skin. In an example, an exchange pump 1300 provides air into the sealable volume 900 (e.g., via the conduits 1102) at a rate that is less than the rate of evacuation of air from the sealable volume 900 by the force generator 1104. Accordingly, the controller 102 may operate the exchange pump 1300 and the force generator 1104 to promote air exchange in the sealable volume 900. In another example, the seal 904 may have a defined leakage to ensure that atmospheric air enters the housing 800 (e.g., the seal 904 allows air to enter the sealable volume 900 at a rate less than what is withdrawn by the force generator 1104). Accordingly, the seal 904 may provide a partial segregation of the volume 900 from the surround environment. In yet another example, a mechanical or electromagnetic valve may partly or fully open, either at programmed intervals (e.g., with the controller), at all times, or in synchronization with physical or physiological parameters. For example, the valve may open when an embedded oxygen sensor or a moisture detector indicates that the oxygen content of the air within the housing 800 is below a threshold.

The controller 102 may operate the force generator 1104 based on motion of the patient 204. For example, the controller 102 may be in communication with a position sensor 1306 (e.g., an accelerometer, inertial reference unit, or the like) that determine one or more kinematic characteristics of the patient 204. The kinematic characteristics of the patient include (but are not limited to) position, velocity, acceleration, or jerk of a portion of the patient, for instance the kinematic characteristics of the limb 202. The controller 102 may compare the determine kinematic characteristics to a kinematic threshold, for instance to determine whether movement of the patient 204 affects blood flow of the patient 204. For example, adduction of the limb 202 may reduce blood flow in the limb 202. The limb 202 may contact the torso of the patient 204, which may compress the vein 300. The controller 102 may operate the force generator 1104 when the determined kinematic characteristics exceed the kinematic threshold.

Certain patient positions and movements may augment or reduce blood flow in the limb veins and, therefore, into the blood circuit connected to the blood filtration system (e.g., an ultrafiltration device). The system may provide feedback to a patient undergoing blood filtration therapy to encourage the patient to maintain limb position and optimize blood flow in the limb. For example, the blood filtration system may use extracorporeal blood flow (e.g. withdrawal pressure, infusion pressure, withdrawal resistance, infusion resistance, withdrawal blood flow, etc.) and annunciator or visual or haptic based incentives, to encourage the patient to maintain a limb position for optimal blood flow from the vein to the extracorporeal circuit and back to the vein. In an example, a patient may move its arm, for example, to a non-optimal position (e.g., where the access resistance increases). The blood filtration system may provide a signal (e.g., visual, audible, haptic, notification, or the like) to the patient (or a healthcare provider) to gently remind the patient (or healthcare provider) to return to an ideal position for maintenance of blood flow.

A catheter protector may be attached to the limb, for instance to help encourage the patient to maintain the limb in a position (e.g. elevation, abduction, rotation, or the like) that helps increase or optimize venous return and helps reduce or minimize resistance to blood flow. The optimal position may differ from patient to patient. The appliance/garment may be "programmable" in the sense that the optimal position is customized and set for each individual patient. For example, an air inflatable pillow(s) may surround the limb in order to set the limb in the optimal position by inflating each individual pillow to varying extents. In an example, the catheter protector may include one or more of the components, features, functions, or the like of the subject matter discussed in PCT application PCT/US2019/068989, which is hereby incorporated by reference herein in its entirety.

For instance, the portable arm support may help maintain continuous blood flow through the patient's blood stream, and the extracorporeal components of the blood filtration system. In an example, the portable arm support may encourage the patient to maintain a preferred body position, for example locating the arm of the patient away from a midline of the body of the patient. For instance, the portable arm support may elevate the arm of the patient (e.g., 15 degrees relative to a foundation surface, such as a bed, couch, or the like). Additionally, the portable arm support may abduct the arm of the patient (e.g., locate the arm away from the torso of the patient). Locating the arm of the patient away from the midline of the patient may help improve blood flow within the blood stream (e.g., the basilic vein) and improved blood flow within the blood stream may reduce clotting within the extracorporeal components of the blood filtration system and accordingly improve the performance of the blood filtration system.

FIG. 14 shows one example of a method 1400 for stimulating blood flow in vasculature of a patient, according to an embodiment of the present subject matter. In describing the method 1400, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1400 include, but are not limited to, the corresponding numbered elements provided herein and other corresponding elements described herein (both numbered and unnumbered) as well as their equivalents.

At 1402, the method 1400 a limb 202 of a patient 204 may be enclosed in a sealable volume 900 of housing 800 of a blood flow stimulator 200. The method 1400 includes at 1404 a pressure differential is generated in the sealable volume 900 relative to a surrounding environment 902 of the blood flow stimulator 200. At 1406, a blood pump 112 of a blood filtration system 100 may be operated to pump blood through a blood circuit 120.

Several options for the method 1400 follow. For example, a catheter 108 may be inserted into vasculature of the patient (e.g., the vein 300, shown in FIG. 3). The catheter 108 may be located with the sealable volume 900 of the housing 800. Accordingly, the blood flow stimulator 200 may stimulate blood flow in the limb 202 of a patient 204 while the blood filtration system 100 reduces one or more plasma constituents in the blood of the patient 204.

Figure 15:
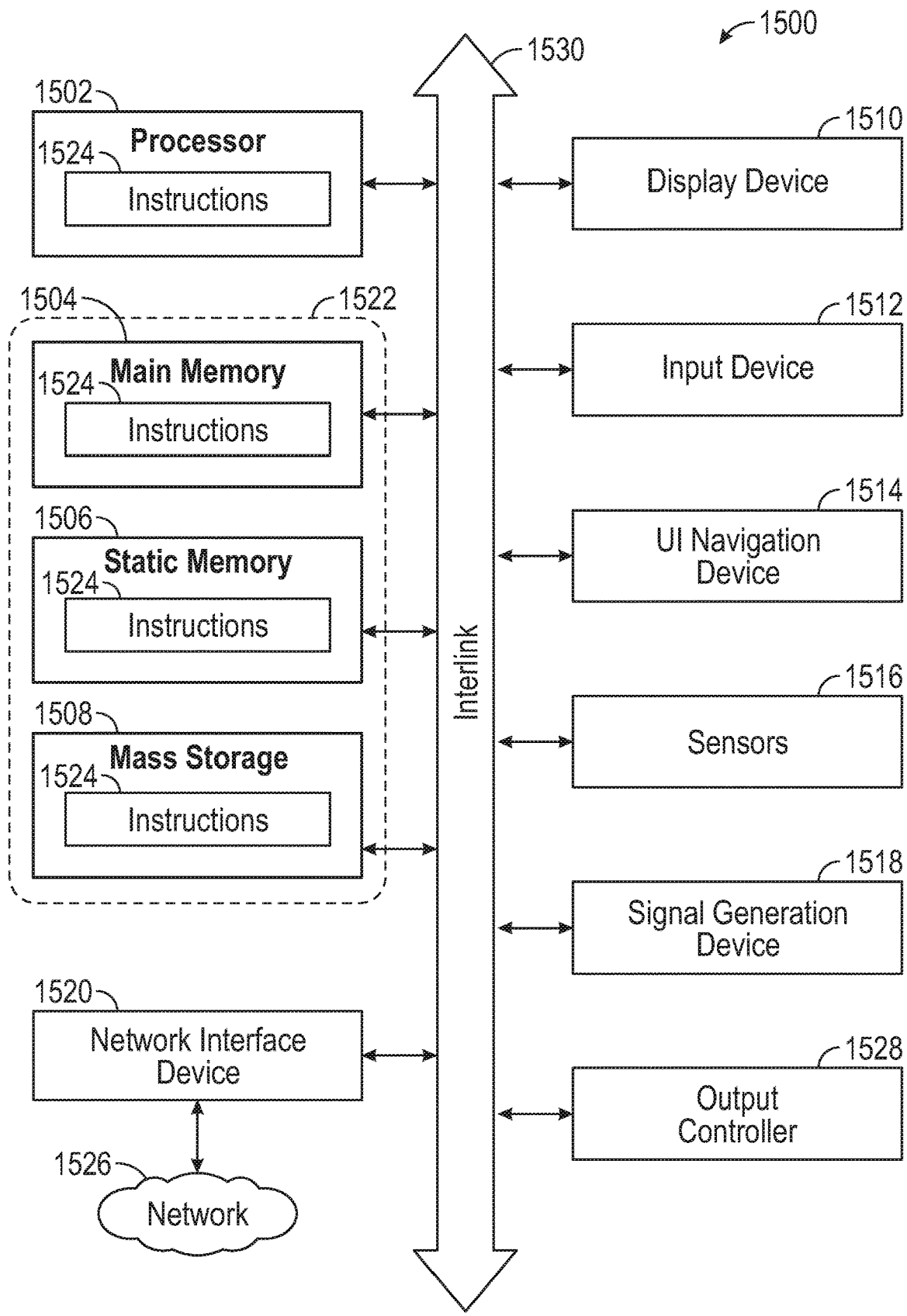
FIG. 15 shows a block diagram of an example machine upon which any one or more of the techniques discussed herein may perform.

FIG. 15 shows a block diagram of an example machine 1500 upon which any one or more of the techniques (e.g., methodologies) discussed herein may perform. Examples, as described herein, may include, or may operate by, logic or a number of components, or mechanisms in the machine 1500. Circuitry (e.g., processing circuitry) is a collection of circuits implemented in tangible entities of the machine 1500 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1500 follow.

In alternative embodiments, the machine 1500 may operate as a standalone device or may be connected (e.g., networked) to other machines. In a networked deployment, the machine 1500 may operate in the capacity of a server machine, a client machine, or both in server-client network environments. In an example, the machine 1500 may act as a peer machine in peer-to-peer (P2P) (or other distributed) network environment. The machine 1500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1500 may include a hardware processor 1502 (e.g., a central processing unit (CPU), a graphics processing unit (GPU), a hardware processor core, or any combination thereof), a main memory 1504, a static memory (e.g., memory or storage for firmware, microcode, a basic-input-output (BIOS), unified extensible firmware interface (UEFI), etc.) 1506, and mass storage 1508 (e.g., hard drive, tape drive, flash storage, or other block devices) some or all of which may communicate with each other via an interlink (e.g., bus) 1530. The machine 1500 may further include a display unit 1510, an alphanumeric input device 1512 (e.g., a keyboard), and a user interface (UI) navigation device 1514 (e.g., a mouse). In an example, the display unit 1510, input device 1512 and UI navigation device 1514 may be a touch screen display. The machine 1500 may additionally include a storage device (e.g., drive unit) 1508, a signal generation device 1518 (e.g., a speaker), a network interface device 1520, and one or more sensors 1516, such as a global positioning system (GPS) sensor, compass, accelerometer, or other sensor. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1502, the main memory 1504, the static memory 1506, or the mass storage 1508 may be, or include, a machine readable medium 1522 on which is stored one or more sets of data structures or instructions 1524 (e.g., software) embodying or utilized by any one or more of the techniques or functions described herein. The instructions 1524 may also reside, completely or at least partially, within any of registers of the processor 1502, the main memory 1504, the static memory 1506, or the mass storage 1508 during execution thereof by the machine 1500. In an example, one or any combination of the hardware processor 1502, the main memory 1504, the static memory 1506, or the mass storage 1508 may constitute the machine readable media 1522. While the machine readable medium 1522 is illustrated as a single medium, the term "machine readable medium" may include a single medium or multiple media (e.g., a centralized or distributed database, and/or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1524 may be further transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communications network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software. A transmission medium is a machine readable medium.

Figure 16:
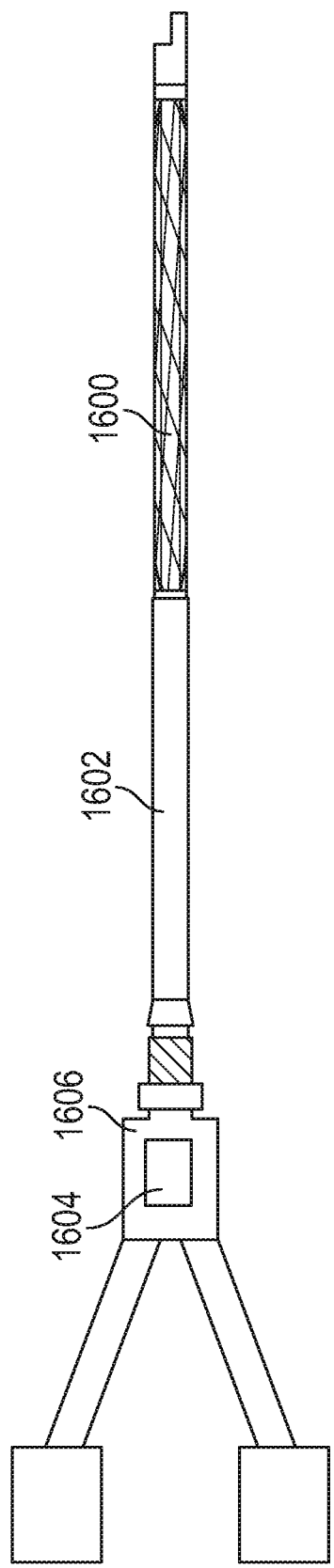
FIG. 16 shows a side view of an example of an adjustable stent for insertion into vasculature of a patient, according to an embodiment of the present subject matter.

FIG. 16 shows a side view of an example of an adjustable stent 1600 for insertion into vasculature of a patient. In an example, the stent 1600 is included in a catheter 1602. In an example, the stent helps enhance blood flow within vasculature of the patient. For instance, the stent 1600 may be located in a vein of a patient. The stent 1600 may enhance blood flow into the catheter 1602, for example by engaging with an interior wall of the vein to expand a diameter of the vein. For example, the stent 1600 helps enhance annular flow between the catheter 1602 and the interior wall of the vein. In some examples, the stent 1600 may generate a volume space between the inner wall of the vein and an outer surface of the catheter 1602, for instance to increase blood flow within the system 100 and the vasculature of the patient. Accordingly, the blood filtration system 100 may reduce venous regional resistance to blood flow within the vasculature of the patient, and may permit a higher volume rate of blood flow to enter the blood circuit 120. Thus, occlusion of the blood circuit 120 is reduced, and performance of the blood filtration system 100 is enhanced.

Figure 17:
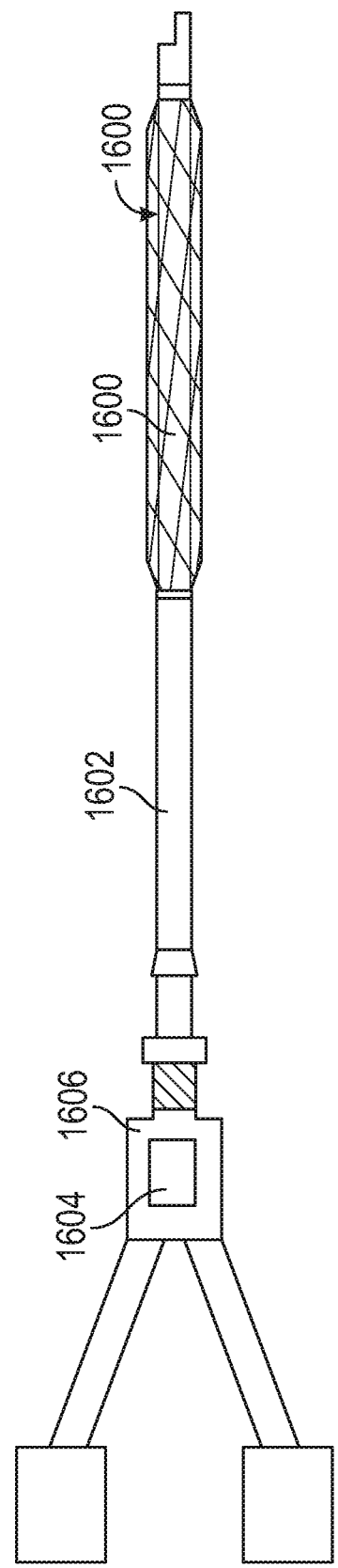
FIG. 17 shows the adjustable stent of FIG. 16 in an expanded configuration, according to an embodiment of the present subject matter.

FIG. 16 shows the adjustable stent 1600 in a collapsed configuration. In the collapsed configuration, the stent 1600 is collapsed against the catheter 1602. FIG. 17 shows the adjustable stent 1600 in an expanded configuration. In the expanded configuration, the stent 1600 projects from the catheter 1602. In an example, the catheter 1602 includes a stent actuator 1604 (e.g., a solenoid, motor, piston, drive circuitry for piezoelectric material, or the like). For instance, the stent actuator 1604 is included in a hub 1606 of the catheter 1602, and the stent actuator 1604 helps facilitate transitioning of the stent 1600 between the collapsed configuration and the expanded configuration. In an example, the stent actuator 1604 displaces the stent 1600 (or a portion of the stent 1600) to expand (or collapse) the stent 1600 relative to the catheter 1602. In some examples, the stent actuator 1604 may include a guidewire coupled with the stent 1600. Displacement of the guidewire relative to the hub 1606 (e.g., by a user manipulating the guidewire, such as by pulling or pushing the guidewire) transitions the stent 1600 between the collapsed configuration and the expanded configuration. The stent actuator 1604 may displace the guidewire relative to the hub 1606 to transition the stent 1600 between the collapsed configuration and the expanded configuration.

In another example, the adjustable stent 1600 includes a piezoelectric material. The stent actuator 1604 may provide an electrical signal to piezoelectric material of the stent 1600 to displace the stent 1600 (e.g., displace the stent 1600 relative to the catheter 1602). Accordingly, the stent actuator 1604 may transition the stent 1600 between collapsed and expanded configurations, such as by selectively energizing the piezoelectric material included in the stent 1600 to displace the stent 1600. In yet another example, an electromagnetic solenoid piston may be coupled to the stent 1600.

Figure 18:
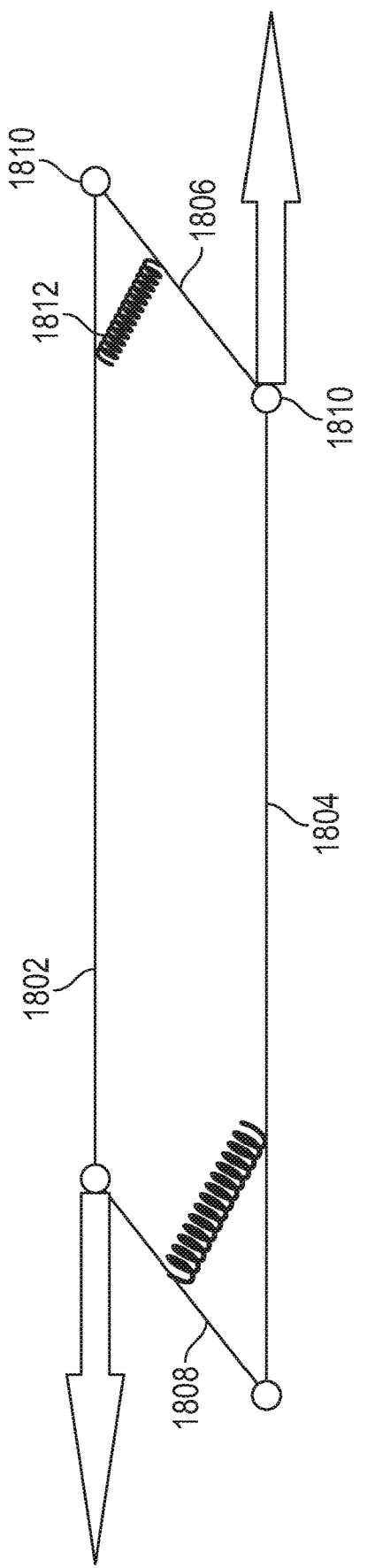
FIG. 18 shows a detailed view of an example of a unit cell for the adjustable stent of FIG. 16, according to an embodiment of the present subject matter.

FIG. 18 shows a detailed view of an example of a unit cell 1800 for the adjustable stent 1600. In an example, the unit cell 1800 includes one or more of a first leg 1802, a second leg 1804, a third leg 1806, or a fourth leg 1808. In an example, the legs 1802, 1804, 1806, 1808 are connected to each other, for instance at a joint 1810 between the leg 1802 and the leg 1806.

In an example, displacement of the legs 1802, 1804, 1806, 1808 changes the shape of the unit cell 1800. For instance, motion of the joints 1810 in the direction indicated by the arrows in FIG. 18 may cause the unit cell 1800 to expand (e.g., bring the leg 1802 remote from the leg 1804). In another example, motion of the joints 1810 in the direction opposite of the arrows in FIG. 18 may cause the unit cell 1800 to contract (e.g., bring the leg 1802 adjacent the leg 1804). The stent 1600 may be in the expanded configuration when the unit cell 1800 is expanded. The stent 1600 may be in the collapsed configuration when the unit cell 1800 is collapsed (e.g., contracted, squeezed, squished, or the like).

In some examples, the unit cell 1800 may be biased toward the expand configuration or the collapsed configuration. For instance, a biasing element 1812 may bias the legs 1802, 1806 together to bias the unit cell to the collapsed configuration. Displacement of the joints 810 (e.g., the joint 810 between legs 1804, 1806) in the direction of the arrow in FIG. 18 may overcome the bias, for instance to transition the unit cell 1800 to the expanded configuration. In another example, material properties of the legs 1802, 1804, 1806, 1808 provide the bias between the legs 1802, 1804, 1806, 1808. For example, the legs 1802, 1804, 1806, 1808 may include an elastic material that facilitates biasing of the unit cell 1800 to the collapsed configuration.

Figure 19:
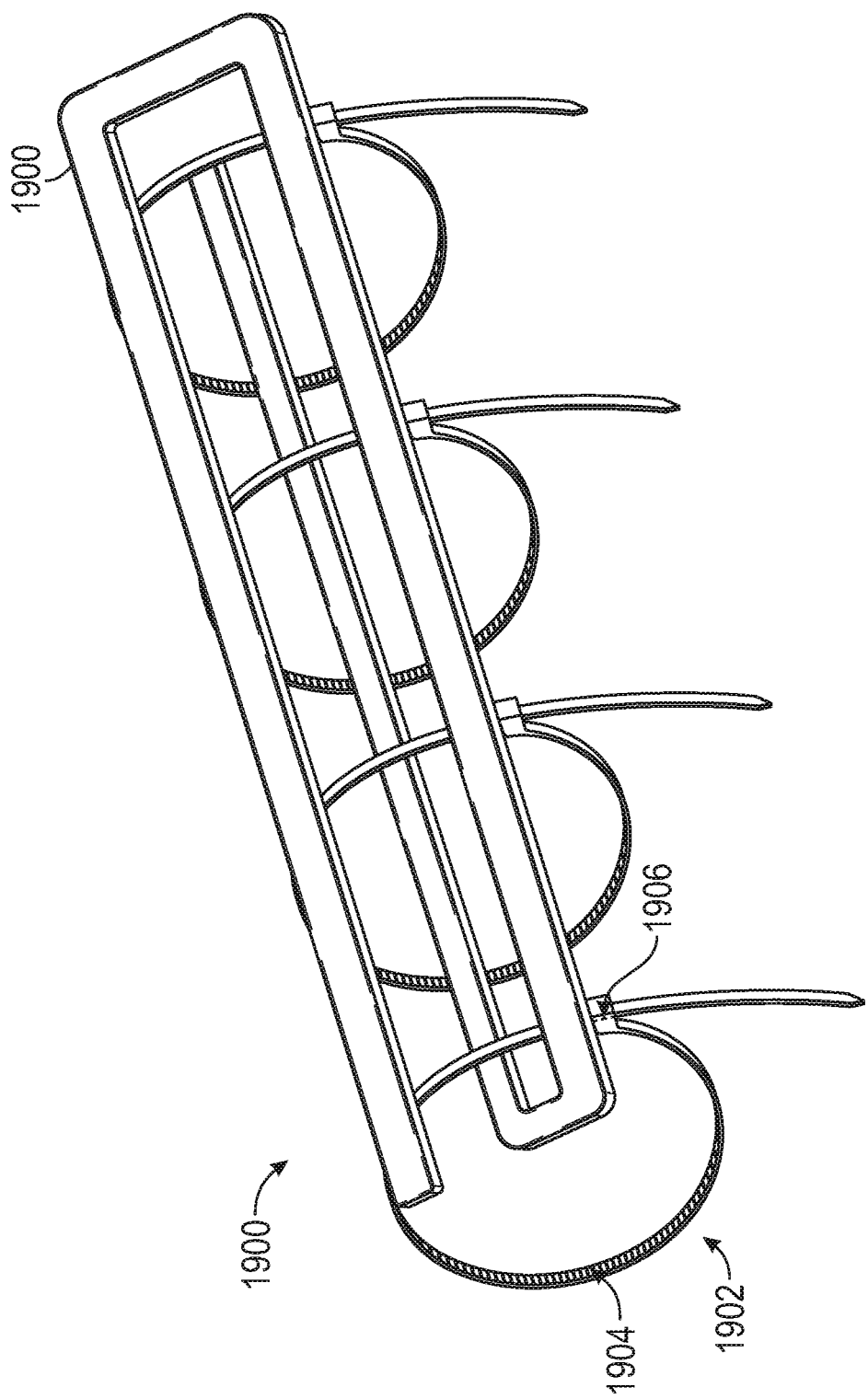
FIG. 19 shows a perspective view of another example of an adjustable stent.

FIG. 19 shows a perspective view of another example of the adjustable stent 1600. In an example, the stent 1600 may include a stent body 1900. The stent 1600 may include one or more bands 1902. The bands 1902 may be adjustable to change a size of the stent 1600, such as a size of the bands 1902. For example, the bands 1902 may include a first set of teeth 1904. The stent body 1900 may include a second set of teeth 1906. The first set of teeth 1904 may correspond with the second set of teeth 1906, for instance to allow the teeth 1904, 1906 to engage with each other. The size of the bands 1902 may be adjusted, for example by displacing the teeth 1904 of the bands 1902 relative to the teeth 1906 of the stent body 1900. In an example, the teeth 1904, 1906 engage in a ratcheting configuration. For instance, the teeth 1904, 1906 may engage with each other at one or more positions to change the size of the bands 1902. Accordingly, the size of the bands 1902 may be adjusted, such as to increase the vein lumen between an outer wall of a catheter and an inner wall of a vein of a patient.

Figure 20:
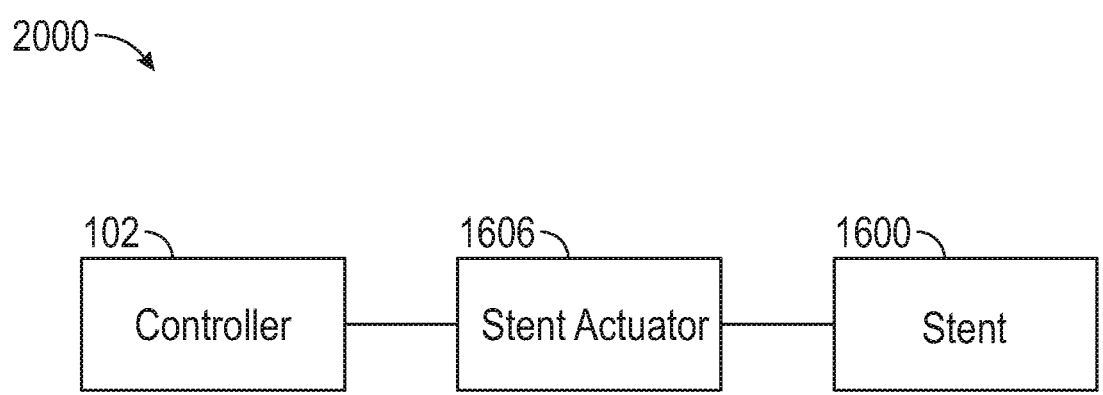
FIG. 20 shows a schematic diagram of an example of a blood filtration system.

FIG. 20 shows a schematic diagram of an example of a blood filtration system 2000. In an example, the blood filtration system 2000 includes one or more components (or functions) of the blood filtration system 100 (shown in FIG. 1). For instance, the system 2000 may include the controller 102. The controller 102 may be in communication with the stent actuator 1604, for example to transition the stent 1600 between the collapsed configuration and the expanded configuration. The controller 102 may modulate the stent actuator 1604, for example to selectively transition the stent 1600 between the collapsed configuration and the expanded configuration.

In an example, the controller 102 modulates the stent actuator 1604 to vary a size of the stent 1600 according to one or more measured characteristics of the system 2000 (or the system 100). In another example, the controller 102 modulates the stent actuator 1604 to vary a size of the stent 1600 according to one or more measured physiological characteristics of a patient (e.g., respiratory rate, heart rate, or the like). For instance, the controller 102 modulates the stent actuator 1604 according to blood flow measurements within the blood circuit 120 (or patient vasculature). For instance, the controller 102 may be in communication with a doppler velocimeter that determines blood flow in vasculature of a patient. The controller 102 may modulate the stent actuator 1604 to increase the size of the stent 1600, for instance when the blood flow rate in the vasculature of the patient exceeds a specified threshold value. In another example, the controller 102 modulates the stent actuator 1604 according to access resistance of the system, withdrawal pressure of a catheter, infusion pressure of a catheter, or the like. For instance, the controller 102 may modulate the stent actuator 1604 to increase the size of the stent 1600 when the access resistance of the system exceeds a specified threshold value. The controller may modulate the stent actuator 1604 to decrease the size of the stent 1600 when the access resistance exceeds the specified threshold value.

In some examples, the controller 102 is in communication with the console 206 (shown in FIG. 2). The controller 102 may cooperate with the console 206 to inform the user to adjust the size of the stent 1600. For example, the controller 102 may provide a notification (e.g., by displaying a message on a display of the console 206) to increase the size of the stent 1600, for instance when the access resistance of the system exceeds a specified threshold value. Accordingly, the blood filtration system 2000 facilitates manual adjustment of the size of the stent (e.g., by a health care provider adjusting the size of the stent 1600) according to measured characteristics of the system 2000, the system 100, or physiological characteristics of a patient.

Example 1 is a blood flow stimulator for encouraging blood flow in a limb of a patient, comprising: a housing configured for sealing about the limb of the patient, the housing including a sealable volume, wherein the housing is configured to receive the limb of the patient within the sealable volume; a seal coupled with the housing and configured to engage with at least a portion of the limb to segregate the sealable volume from a surrounding environment of the blood flow stimulator; and a conduit extending through the housing, wherein the conduit provides access to the sealable volume from the surrounding environment.

In Example 2, the subject matter of Example 1 optionally includes a force generator configured to generate a force upon skin of the limb to encourage blood flow in the limb when the limb is received in the sealable volume.

In Example 3, the subject matter of Example 2 optionally includes wherein the force generator includes a pump configured to generate a pressure differential within the sealable volume.

In Example 4, the subject matter of any one or more of Examples 2-3 optionally include wherein the force generator includes one or more of an adhesive, or a suction cup.

In Example 5, the subject matter of any one or more of Examples 2-4 optionally include wherein the force generator is in communication with the conduit.

In Example 6, the subject matter of any one or more of Examples 2-5 optionally include a controller including processing circuitry configured to operate the force generator to generate the force upon the skin of the patient.

In Example 7, the subject matter of Example 6 optionally includes wherein the controller modulates the force generator in correspondence with one or more physical or physiological parameters.

In Example 8, the subject matter of Example 7 optionally includes wherein the controller modulates the force generator in correspondence with a respiratory cycle of the patient.

In Example 9, the subject matter of any one or more of Examples 1-8 optionally include a blood circuit, wherein the conduit is configured to receive a portion of the blood circuit.

In Example 10, the subject matter of any one or more of Examples 1-9 optionally include wherein the housing includes an open configuration and a closed configuration, the housing including: a first housing segment; a second housing segment; and a hinge moveably interconnecting the first housing segment with the second housing segment, wherein the hinge facilitates transitioning the housing between the open configuration and the closed configuration.

In Example 11, the subject matter of Example 10 optionally includes a locking mechanism configure to maintain the housing in a locked configuration and secure.

In Example 12, the subject matter of any one or more of Examples 1-11 optionally include wherein: the sealable volume is segregated into a first section and a second section; the conduit is a first conduit, and the first conduit is in communication with the first section of the sealable volume; and the blood flow stimulator includes a second conduit in communication with the second section of the sealable volume.

Example 13 is a blood filtration system, comprising: a blood flow stimulator for encouraging blood flow in a limb of a patient, including: a housing including a sealable volume, wherein the housing is configured to receive the limb of the patient within the sealable volume; a seal coupled with the housing and configured to engage with the limb to segregate the sealable volume from a surrounding environment of the blood flow stimulator; a force generator configured to generate a force upon skin of the limb to encourage blood flow in the limb when the limb is received in the sealable volume; and a controller including processing circuitry configured to operate the force generator to generate the force applied to the skin of the patient.

In Example 14, the subject matter of Example 13 optionally includes a conduit extending through the housing, wherein the conduit provides access to the sealable volume from the surrounding environment.

In Example 15, the subject matter of any one or more of Examples 13-14 optionally include wherein the blood filtration system is configured to reduce one or more plasma constituents in blood of a patient.

In Example 16, the subject matter of any one or more of Examples 13-15 optionally include wherein the controller is further configured to: operate the force generator to generate the force upon the skin of the patient.

In Example 17, the subject matter of Example 16 optionally includes wherein force generator includes a pump, and operation of the pump generates a pressure differential in the sealable volume relative to the surrounding environment.

In Example 18, the subject matter of any one or more of Examples 13-17 optionally include wherein the controller is further configured to: modulate the force generator in correspondence with one or more physical or physiological parameters.

In Example 19, the subject matter of any one or more of Examples 13-18 optionally include wherein the controller modulates the force generator in correspondence with a respiratory cycle of the patient.

In Example 20, the subject matter of Example 19 optionally includes wherein the controller modulates the force generator to increase the force applied to the skin of the patient during inspiration by the patient.

In Example 21, the subject matter of any one or more of Examples 19-20 optionally include wherein the controller modulates the force generator to decrease the force applied to the skin of the patient during expiration by the patient.

In Example 22, the subject matter of any one or more of Examples 13-21 optionally include a respiratory sensor configured to determine a respiratory cycle of the patient.

In Example 23, the subject matter of Example 22 optionally includes wherein the controller is in communication with the respiratory sensor and the controller is further configured to: monitor the respiratory cycle of the patient.

In Example 24, the subject matter of any one or more of Examples 13-23 optionally include wherein: the blood flow stimulator includes: a first section of the sealable volume segregated from a second section of the sealable volume; a first conduit in communication with the first section of the sealable volume; a second conduit in communication with the second section of the sealable volume; and wherein the first conduit and the second conduit facilitate pressurizing the first section independent of the second section; and the controller is configured to: operate the force generator to pressurize the first section of the sealable volume at a first pressure; operate the force generator to pressurize the second section of the sealable volume at a second pressure.

In Example 25, the subject matter of Example 24 optionally includes wherein the controller is configured to: drive venous return through a vein of the patient by modulating the force generator to vary the pressure in the first section and the second section of the sealable volume.

In Example 26, the subject matter of any one or more of Examples 13-25 optionally include wherein the blood filtration system includes a kinematic sensor configured to determine kinematic characteristics of the limb of the patient, and wherein the controller is configured to: monitor the kinematic characteristics of the limb; compare the monitored kinematic characteristics to a kinematic threshold; and operate the force generator when the monitored kinematic characteristics exceed the kinematic threshold.

Example 27 is a method for stimulating blood flow in vasculature of a patient, comprising: enclosing a limb of a patient in a sealable volume of a housing of a blood flow stimulator; generating a pressure differential in the sealable volume relative to a surround environment of the blood flow stimulator; and operating a blood pump of a blood filtration system to pump blood through a blood circuit, wherein the blood filtration system is configured to reduce one or more plasma constituents in blood of a patient.

In Example 28, the subject matter of Example 27 optionally includes inserting a catheter into vasculature of the patient.

In Example 29, the subject matter of Example 28 optionally includes locating the catheter within the sealable volume of the housing.

Example 30 is a blood filtration system, comprising: a blood flow stimulator for encouraging blood flow in a limb of a patient, the blood flow stimulator including: an adjustable stent configured to engage with vasculature of a patient and enhance flow of blood within the vasculature by expanding a dimension of the vasculature, the stent including: a collapsed configuration; an expanded configuration, wherein a size of the stent in the expanded configuration is greater than the size of the stent in the collapsed configuration; a stent operator configured to transition the adjustable stent between the collapsed configuration and the expanded configuration; a controller, including processing circuitry, configured to: modulate the stent operator to vary the size of the stent.

In Example 31, the subject matter of Example 30 optionally includes a catheter, wherein the stent is configured to increase a volume space between an inner wall of the vasculature and an outer wall of the catheter.

In Example 32, the subject matter of any one or more of Examples 30-31 optionally include further comprising a catheter, wherein the controller is configured to: determine one or more of access resistance of the system, withdrawal pressure of the catheter, infusion pressure of the catheter, or respiratory cycle of a patient; compare the access resistance, withdrawal pressure, infusion pressure, or respiratory cycle to a specified threshold value; and modulate the stent to vary the size of the stent when the access resistance, withdrawal pressure, infusion pressure, or respiratory cycle exceeds the specified threshold value.

In Example 33, the subject matter of Example 32 optionally includes wherein the controller is configured to increase the size of the stent when the access resistance, withdrawal pressure, infusion pressure, or respiratory cycle exceeds the specified threshold value.

In Example 34, the subject matter of any one or more of Examples 32-33 optionally include wherein the controller is configured to decrease the size of the stent when the access resistance, withdrawal pressure, infusion pressure, or respiratory cycle exceeds the specified threshold value.

In Example 35, the subject matter of any one or more of Examples 30-34 optionally include wherein the blood flow stimulator is a first blood flow stimulator, and further comprising: a second blood flow stimulator for encouraging blood flow in a limb of a patient, including: a housing including a sealable volume, wherein the housing is configured to receive the limb of the patient within the sealable volume; and a seal coupled with the housing and configured to engage with the limb to segregate the sealable volume from a surrounding environment of the blood flow stimulator; a force generator configured to generate a force upon skin of the limb to encourage blood flow in the limb when the limb is received in the sealable volume; and wherein the controller is configured to operate the force generator to generate the force applied to the skin of the patient.

In Example 36, the subject matter of Example 35 optionally includes further comprising a catheter, wherein the controller is further configured to: determine one or more of access resistance of the system, withdrawal pressure of the catheter, infusion pressure of the catheter, or respiratory cycle of a patient; compare the access resistance, withdrawal pressure, infusion pressure, or respiratory cycle to a specified threshold value; and modulate one or more of the stent or the force generator to vary the one or more of the size of the stent or the force applied by the force generator when the access resistance, withdrawal pressure, infusion pressure, or respiratory cycle exceeds the specified threshold value.

Example 37 may include or use, or may optionally be combined with any portion or combination of any portions of any one or more of Examples 1 through 36 to include or use, subject matter that may include means for performing any one or more of the functions of Examples 1 through 36, or a machine-readable medium including instructions that, when performed by a machine, cause the machine to perform any one or more of the functions of Examples 1 through 36.

Each of these non-limiting examples may stand on its own, or may be combined in various permutations or combinations with one or more of the other examples.

The above description includes references to drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. A blood flow stimulator for encouraging blood flow in a limb of a patient, comprising:
   a housing configured for sealing about the limb of the patient, the housing including a sealable volume, wherein the housing is configured to receive the limb of the patient within the sealable volume;
   a first seal coupled with the housing and configured to engage with at least a portion of the limb to segregate the sealable volume from a surrounding environment of the blood flow stimulator;

a second seal within the sealable volume and configured to engage with at least a second portion of the limb to segregate the sealable volume into a first section and a second section;
a first conduit extending through the housing, wherein:
the first conduit provides access to the sealable volume from the surrounding environment; and
the first conduit is configured to receive a portion of a blood filtration circuit that is external of the patient;
a second conduit extending through the housing and in communication with the first section of the sealable volume;
a third conduit extending through the housing and in communication with the second section of the sealable volume; and
a force generator configured for communication with the second conduit and the third conduit, wherein the force generator is configured to generate a pressure differential within the sealable volume, and is configured to generate a force upon skin of the limb to encourage blood flow in the limb when the limb is received in the sealable volume.

2. The blood flow stimulator of claim 1, wherein the force generator includes a pump configured to generate a pressure differential within the sealable volume.

3. The blood flow stimulator of claim 1, wherein the force generator includes one or more of an adhesive, or a suction cup.

4. The blood flow stimulator of claim 1, further comprising a controller including processing circuitry configured to operate the force generator to generate the force upon the skin of the patient.

5. The blood flow stimulator of claim 4, wherein the controller modulates the force generator in correspondence with one or more physical or physiological parameters.

6. The blood flow stimulator of claim 5, wherein the controller modulates the force generator in correspondence with a respiratory cycle of the patient.

7. The blood flow stimulator of claim 1, further comprising the blood filtration circuit.

8. The blood flow stimulator of claim 1, wherein the housing includes an open configuration and a closed configuration, the housing including:
a first housing segment;
a second housing segment; and
a hinge moveably interconnecting the first housing segment with the second housing segment, wherein the hinge facilitates transitioning the housing between the open configuration and the closed configuration.

9. The blood flow stimulator of claim 8, further comprising:
a locking mechanism configure to maintain the housing in a locked configuration and secure.

* * * * *